(12) United States Patent
Booth et al.

(10) Patent No.: US 10,206,481 B2
(45) Date of Patent: *Feb. 19, 2019

(54) BAKED POWDER PENCILS, STICKS AND PELLETS, AND METHODS OF MAKING AND USING THE SAME

(71) Applicant: Cosmetic Group USA, Inc., Sun Valley, CA (US)

(72) Inventors: Alfred E. Booth, Sun Valley, CA (US); Jeff Ellery Engels, Castaic, CA (US)

(73) Assignee: COSMETIC GROUP USA, INC., Sun Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,878

(22) Filed: Jun. 16, 2017

(65) Prior Publication Data

US 2017/0280854 A1    Oct. 5, 2017

Related U.S. Application Data

(62) Division of application No. 14/860,447, filed on Sep. 21, 2015, now Pat. No. 9,700,120.

(Continued)

(51) Int. Cl.
*A45D 40/12* (2006.01)
*A61K 8/02* (2006.01)
(Continued)

(52) U.S. Cl.
CPC ........ *A45D 40/12* (2013.01); *A45D 2040/208* (2013.01); *A61K 8/022* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 4,414,200 | A | 11/1983 | Murphy et al. |
| 4,587,072 | A | 5/1986 | Ohtomo et al. |

(Continued)

FOREIGN PATENT DOCUMENTS

| | | |
|---|---|---|
| EP | 0 617 905 | 10/1994 |
| EP | 2 220 959 | 8/2010 |

(Continued)

OTHER PUBLICATIONS

International Search Report and Written Opinion dated Jan. 11, 2016, for application No. PCT/US2015/051282.

(Continued)

*Primary Examiner* — David Walczak
(74) *Attorney, Agent, or Firm* — Foley & Lardner LLP

(57) ABSTRACT

A baked powder pencil includes a housing having a base portion with a hollow interior and an opening that opens into the hollow interior. A stick or pellet of baked powder cosmetic material is disposed at least partially within the hollow interior of the base portion. The stick or pellet of baked powder cosmetic material has an end portion that is arranged to extend through the opening of the base portion. The stick or pellet of baked powder cosmetic material is formed into a pre-defined three-dimensional shape and is configured to maintain its three-dimensional shape. The three-dimensional shape of the stick or pellet may have a head section with multiple, generally planar surfaces extending in multiple respectively different planes, or a head section with a semi-spherical or semi-spheroid shape.

23 Claims, 15 Drawing Sheets

Related U.S. Application Data

(60) Provisional application No. 62/053,690, filed on Sep. 22, 2014.

(51) Int. Cl.
*A61Q 1/02* (2006.01)
*A45D 40/20* (2006.01)

(52) U.S. Cl.
CPC .......... *A61K 8/0216* (2013.01); *A61K 8/0229* (2013.01); *A61Q 1/02* (2013.01)

(56) References Cited

U.S. PATENT DOCUMENTS

| | | |
|---|---|---|
| 4,820,070 A | 4/1989 | Spatz |
| 5,902,062 A | 5/1999 | Rosenblatt et al. |
| 7,891,896 B2 | 2/2011 | Nasu |
| 2008/0050169 A1 | 2/2008 | Nasu |
| 2009/0142382 A1 | 6/2009 | Shah et al. |

FOREIGN PATENT DOCUMENTS

| | | |
|---|---|---|
| KR | 1020090040027 A | 4/2009 |
| WO | WO-02/072046 A2 | 9/2002 |

OTHER PUBLICATIONS

U.S. Notice of Allowance dated Mar. 10, 2017, from related U.S. Appl. No. 14/860,447.
U.S. Office Action dated Dec. 8, 2016, from related U.S. Appl. No. 14/860,447.
Extended European Search Report dated Mar. 8, 2018, from application No. 15843762.4.
Examination Report dated Aug. 22, 2018, from Brazilian application No. NC2017/0003639.
Colombian Office Action dated Dec. 5, 2018, from application No. NC2017/0003639.
Extended European Search Report dated Nov. 21, 2018, from application No. 18188578.1.

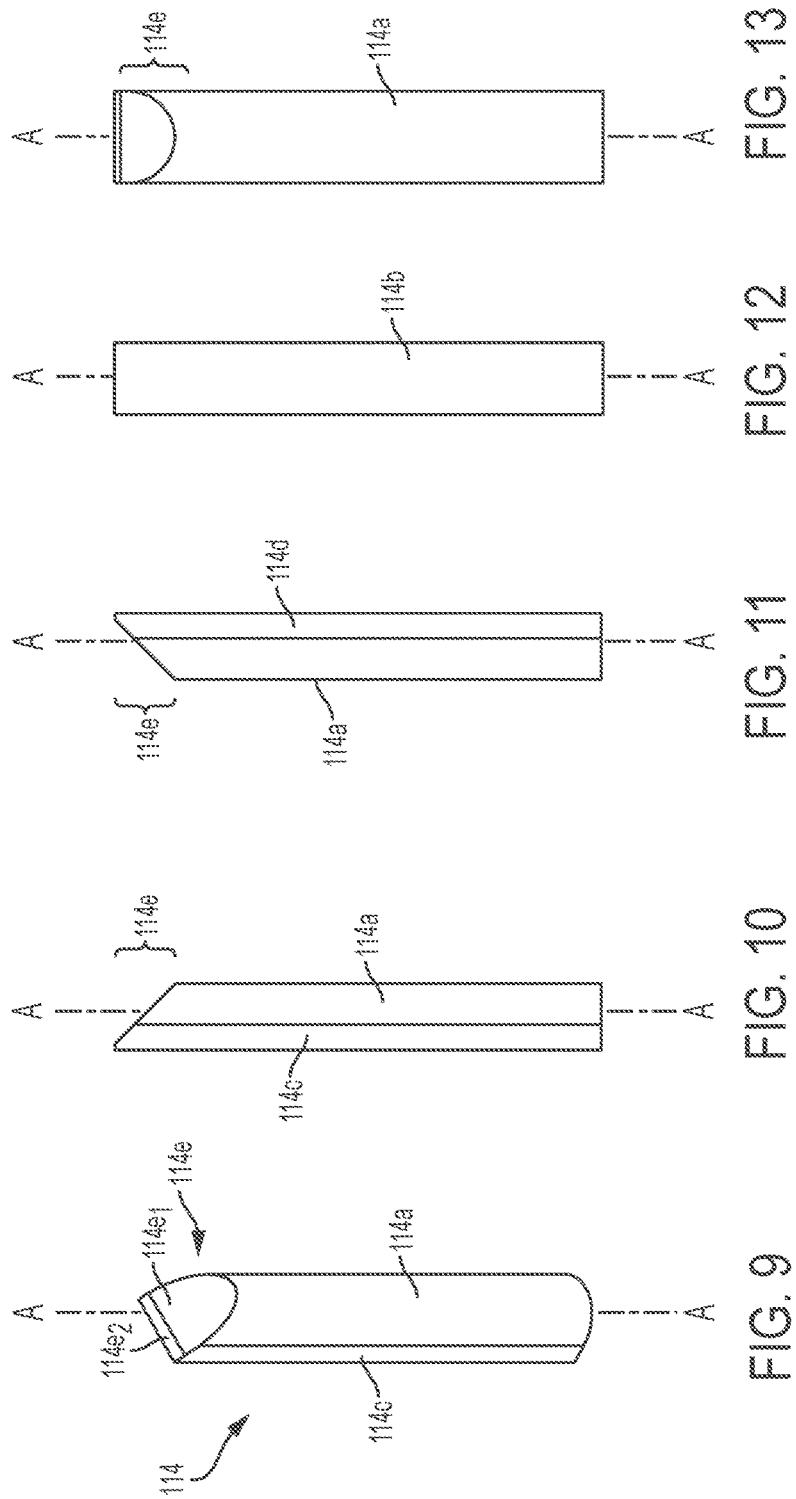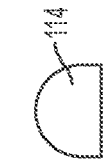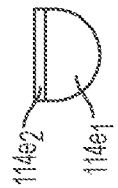

BAKED POWDER PENCILS, STICKS AND PELLETS, AND METHODS OF MAKING AND USING THE SAME

CROSS-REFERENCE TO RELATED APPLICATION

This application is a Divisional of U.S. Pat. No. 9,700,120, granted Jul. 11, 2017, which claims the benefit of U.S. Provisional Patent Application No. 62/053,690, filed Sep. 22, 2014, the entire contents of which are fully incorporated herein by reference in their entirety.

BACKGROUND

Baked powder cosmetics have been made in a variety of colors, for example, to apply as eye shadow or face powder. Various manufacturers produce baked powder cosmetics, typically packaged in a tray (single or multi-compartment) or small, thin container (compact). In such products, baked powder material is held within the confines of the walls of the tray or container, with an upper surface of the baked powder material exposed. The tray or container may include a cap or cover that can selectively cover the upper surface of the baked powder material. When the cap or cover is open, the upper surface of the baked powder is exposed and accessible to the user.

Such baked powder cosmetics are typically applied to a user's face, with an application brush or the user's fingers. In particular, a user can rub a brush (or other applying tool) onto the exposed upper surface of the baked powder in the tray or container, and then rub the brush (or other tool) onto a selected location of the user's face.

The thin trays or compact containers typically used for baked powder cosmetics can be relatively cumbersome to use and can require two hands (one for holding the tray or compact container, and another for holding the application brush or other tool). In addition, such thin trays or compact containers can be relatively messy to use, in that some of the baked powder material can be brushed out of the compartment or onto the housing of the tray or container during use.

In addition, the manner in which the baked powder is applied to the user's face can be limited by the type of brush or other tool (or finger) that the user employs to apply the baked powder.

SUMMARY

Embodiments described herein relate to a baked powder pencil, in which a baked powder material is formed in a stick or pellet shape and is held within a generally cylindrical (or pencil-shaped) housing. The housing is configured to hold the baked powder stick or pellet in a manner that exposes an end portion (including an end surface and at least a portion of a side or peripheral surface) of the stick or pellet.

According to an embodiment, a baked powder pencil includes a housing having a base portion with a hollow interior and an opening that opens into the hollow interior. A stick or pellet of baked powder cosmetic material is disposed at least partially within the hollow interior of the base portion. The stick or pellet of baked powder cosmetic material has an end portion that is arranged to extend through the opening of the base portion.

In particular embodiments, the stick or pellet of baked powder cosmetic material is formed into a pre-defined three-dimensional shape and is configured to maintain its three-dimensional shape without external support.

In particular embodiments, the stick or pellet of baked powder cosmetic material is formed into a pre-defined three-dimensional, generally cylindrical shape having a head section to be applied to a user's skin and a distal end section that is held within the hollow interior of the base portion of the housing.

In particular embodiments, the stick or pellet of baked powder cosmetic material comprises a three-dimensional molded, extruded or shaped body of baked powder material.

In particular embodiments, the base portion of the housing includes at least one projection arranged adjacent the opening of the base portion, the at least one projection arranged to project into a body section of the stick or pellet of baked powder cosmetic material.

In particular embodiments, the base portion of the housing includes a moving mechanism configured to selectively move the stick or pellet of baked powder cosmetic material through the opening of the base portion to adjust a distance that the stick or pellet of baked powder cosmetic material extends past the opening of the base portion of the housing.

In particular embodiments, the moving mechanism is configured to selectively move the stick or pellet of baked powder material in one direction to selectively extend the stick or pellet of baked powder cosmetic material further past the opening of the base portion housing and inhibits movement of the stick or pellet of baked powder cosmetic material in an opposite direction that would retract the stick or pellet of baked powder cosmetic material further into the base portion of the housing.

In particular embodiments, the base portion of the housing includes at least one projection arranged adjacent the opening of the base portion, the at least one projection arranged to project into a body section of the stick or pellet of baked powder cosmetic material; and the moving mechanism is configured to selectively move the stick or pellet of baked powder cosmetic material in one direction to selectively extend the stick or pellet of baked powder cosmetic material further past the opening of the base portion housing and inhibits movement of the stick or pellet of baked powder cosmetic material in an opposite direction that would retract the stick or pellet of baked powder cosmetic material further into the base portion of the housing.

In particular embodiments, the at least one projection is configured with a shape that allows movement of the stick or pellet of baked powder cosmetic material in the one direction and inhibits movement of the stick or pellet of baked powder cosmetic material in the opposite direction.

In particular embodiments, the at least one projection has a tapered surface facing into the base portion of housing, the tapered surface arranged to cut into the body section of the stick or pellet of baked powder material as the stick or pellet of baked powder cosmetic material is moved in the one direction.

Particular embodiments relate to a baked powder cosmetic including a baked powder cosmetic material formed in a stick or pellet having a three-dimensional shape and configured to maintain its three-dimensional shape without external support.

In particular embodiments, the three-dimensional shape of the stick or pellet of baked powder cosmetic material comprises a head section having multiple, generally planar surfaces extending in multiple respectively different planes.

In particular embodiments, the multiple different planes extend at multiple different respective oblique angles relative to each other.

In particular embodiments, the three-dimensional shape of the stick or pellet of baked powder cosmetic material comprises a body section having a generally cylindrical or semi-cylindrical surface extending along an axis A, and wherein the multiple planes extend at multiple different respective oblique angles relative to the axis A.

In particular embodiments, the three-dimensional shape of the stick or pellet of baked powder cosmetic material comprises a head section having a semi-spherical or semi-spheroid shaped surface configured to be applied to a user's skin.

Further embodiments relate to a method of making a baked powder cosmetic including forming a baked powder cosmetic material in a stick or pellet having a three-dimensional shape and configured to maintain its three-dimensional shape without external support; and supporting the stick or pellet in a housing, with a head section of the stick or pellet extending through an opening in the housing, while a body portion of the stick or pellet is contained within the housing.

In particular embodiments, forming the baked powder cosmetic material in a stick or pellet having a three-dimensional shape comprises forming a head section of the stick or pellet, the head section having a semi-spherical or semi-spheroid shaped surface configured to be applied to a user's skin.

In particular embodiments, forming the baked powder cosmetic material in a stick or pellet having a three-dimensional shape comprises forming a head section of the stick or pellet, the head section having multiple, generally planar surfaces extending in multiple respectively different planes.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the various embodiments.

FIGS. 9-15 are perspective, right side, left side, back, front, top and bottom views of a baked powder stick or pellet according to a further embodiment of the present invention.

DETAILED DESCRIPTION

Figure 1:
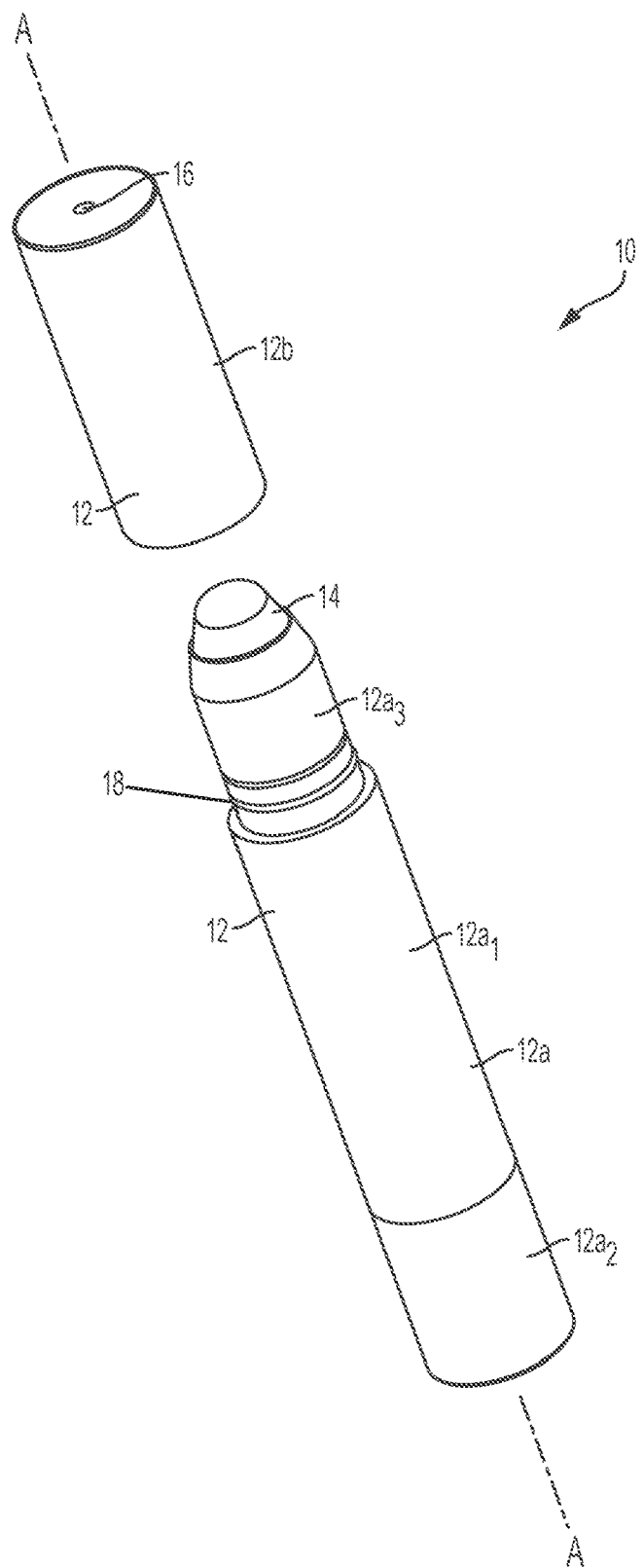
FIG. 1 is a perspective view of a baked powder pencil according to an embodiment.
Figure 2A:
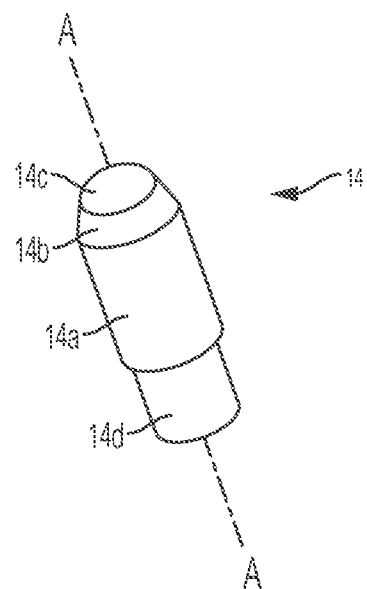
FIGS. 2a-2d are perspective, side, top and bottom views of a baked powder stick or pellet according to an embodiment of the present invention.
Figure 2B:
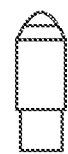
Figure 2C:
Figure 2D:

Various embodiments will be described in detail with reference to the accompanying drawings. Wherever possible, the same reference numbers may be used throughout the drawings to refer to the same or like parts. Different reference numbers may be used to refer to different, same, or similar parts. References made to particular examples and implementations are for illustrative purposes, and are not intended to limit the scope of the invention or the claims.

Embodiments described herein relate to baked powder pencils (and components thereof), in which a baked powder material is formed in a stick or pellet shape and is held within a generally cylindrical (or pencil-shaped) housing. Further embodiments relate to methods of making and using such baked powder pencils and components thereof.

In particular embodiments, the housing is configured to hold the baked powder stick or pellet in a manner that exposes an end portion (including an end surface and at least a portion of a side or peripheral surface) of the baked powder stick or pellet. The housing includes a cover that selectively fits over the exposed end portion of the baked powder stick or pellet, and is selectively removed to allow access to the exposed end portion of the baked powder stick or pellet. When the cover is removed, the housing may be held (for example, in one hand) and brought close to the user's face (or other skin area), to bring the exposed end portion of the baked powder stick or pellet into contact with the user's face (or other skin area). By gripping and moving the housing, the user may wipe or dab the exposed end portion of the baked powder stick or pellet along desired locations on the user's face (or other skin area), to transfer a portion of the baked powder onto the desired locations of the user's face (or other skin area) in a controlled manner.

A baked powder pencil 10 according to an example embodiment is shown in FIGS. 1-7. The baked powder pencil 10 includes a housing 12 and a baked powder stick or pellet 14. The housing 12 includes a base portion 12a and a cap portion 12b. The housing 12 is shown in the perspective view of FIG. 1, with the cap portion 12b removed and separated from the base portion 12a. The housing 12 is shown in the cross-section view of FIG. 4, with the cap portion 12b covering the baked powder stick or pellet 14 and secured to the base portion 12a.

The baked powder stick or pellet 14 is held by the base portion 12a of the housing 12, with at least a portion of the baked powder stick or pellet 14 extending out from one end of the housing 12. In particular embodiments, the base portion 12a of the housing 12 contains components for retaining the baked powder stick or pellet 14 and, in some embodiments, for selectively increasing (or decreasing, or both) the distance that the baked powder stick or pellet 14 extends from the base portion 12a of the housing 12.

In the embodiment of FIG. 1, the base portion 12a of the housing 12 has a hollow, generally cylindrical shape. In the illustrated embodiment, the cylindrical shape of the base portion 12a has a generally circular cross-section, taken perpendicular to and centered on an axis A. In other embodiments, the cylindrical shape of the base portion 12a has other suitable cross-section shapes, such as, but not limited to, triangular, rectangular, hexagonal or other polygonal shape, or an oval or other closed curve shape, or a combination thereof. In further embodiments, the cross-section of the base portion 12a may have different shapes at different locations along the longitudinal axis A.

In the embodiment of FIG. 1, the cap portion 12b of the housing 12 has a hollow, generally cylindrical shape that corresponds to the generally cylindrical shape of the base portion 12a of the housing 12. The cap portion 12b has an open end (facing out of view in FIG. 1) and a hollow interior. The cap portion 12b is configured to fit over and cover the exposed portion of the baked powder stick or pellet 14, to protect the exposed portion of the baked powder stick or pellet 14. The cap portion 12b is also configured to be selectively removed, to allow access to the exposed portion of the baked powder stick or pellet 14. In particular embodiments, the cap portion 12b includes one or more vent openings 16 that open to the hollow interior of the cap portion 12b, for example, to equalize pressure between the interior and exterior environment of the cap portion 12b.

In the embodiment of FIG. 1, the base portion 12a of the housing 12 has a larger diameter section (made of two components $12a_1$ and $12a_2$) and a smaller diameter section $12a_3$. The smaller diameter portion $12a_3$ is dimensioned to fit through the open end of the cap portion 12b and into the hollow interior of the cap portion 12b, when the cap portion 12b is fitted over the exposed portion of the baked powder stick or pellet 14.

In particular embodiments, the cap portion 12b and the base portion 12a, or both, include a mechanism for securing the cap portion 12b to the base portion 12a, when the cap portion 12b is fitted over the exposed portion of the baked powder stick or pellet 14. In the illustrated embodiment, the housing portion 12a includes one or more raised members 18 (such as, but not limited to ribs, o-rings or other raised features) provided on the outer surface of the smaller diameter portion $12a_3$ (around the axis A). The one or more raised members 18 are configured to frictionally engage an inner surface of the cap portion 12b, when the cap portion 12b is placed over the exposed end of the powder stick or pellet 14. In particular embodiments, the frictional engagement provides sufficient friction force to secure the cap portion 12b to the base portion 12a of the housing 12, yet allow selective manual removal of the cap portion 12b from the base portion 12a (for example, by manually pulling the cap portion 12b and base portion 12a apart in opposite directions along the axis A, with sufficient force to overcome the frictional engagement force and separate the cap portion 12b from the base portion 12a.

In the embodiment of FIG. 1, two raised members 18 are shown. In other embodiments, one or more than two raised members 18 are employed to secure the cap portion 12b to the base portion 12a, yet allow selective manual removal of the cap portion 12b from the base portion 12a. In other embodiments, other suitable securing mechanisms are employed to secure the cap portion 12b to the base portion 12a, yet allow selective manual removal of the cap portion 12b from the base portion 12a, where such other securing mechanisms include, but are not limited to other friction fitting surfaces of the cap portion 12b and the base portion 12a, mating screw threads on the cap portion 12b and the base portion 12a, slot and tab connectors, or the like.

The base portion 12a and the cap portion 12b of the housing 12 may be made of any suitable material having sufficient rigidity to operate as described herein, where such material may include, but is not limited to plastic, metal, ceramic, composite material, wood, or any combination thereof. In particular embodiments, the base portion 12a and the cap portion 12b are made of the same material (same type of material). In other embodiments, the base portion 12a is made of a different material than the cap portion 12b. In further embodiments, different sections of the base portion 12a may be made of different materials relative to each other.

An example embodiment of a baked powder stick or pellet 14 is shown in FIGS. 2a-2d. The baked powder stick or pellet 14 is composed of a baked powder material that is pressed into a desired shape. In particular embodiments, any suitable baked powder material that, when pressed and baked, holds a three-dimensional shape without lateral support may be employed.

The baked powder material includes one or more colorants or coloring agents to provide a cosmetic material of a desired color and tone (or of multiple desired colors or tones). In further embodiments, the baked powder material may also include one or more of a skin care agent, a binding agent, or other components. I.

The baked powder stick or pellet 14 is formed into a desired three-dimensional shape by pressing the baked powder material with sufficient pressure and heat, in a mold or shaped tray. In other embodiments, the baked powder stick or pellet is formed by extrusion or molding processes. In other embodiments, other suitable processes for forming a baked powder stick or pellet 14 may be employed. In particular embodiments, the baked powder stick or pellet 14 is configured to maintain its three-dimensional shape without external support, such that the baked powder stick or pellet 14 can stored and transported in that shape, and be placed within and held by a base portion 12a of a housing 12 to assemble a baked powder pencil 10, as described herein. In further embodiments, the baked powder stick or pellet 14 is configured to maintain the three-dimensional shape of a head section (e.g., head section 14c) of the baked powder stick or pellet 14, while a body and distal end section (e.g. body section 14a and distal end section 14d) are supported within the base portion 12a of the housing 12. In such further embodiments, the body portion 12a of the housing 12 may be configured to provide a sufficiently close or snug fit with the body and distal end sections (e.g., body section 14a and distal end section 14d) of the baked powder stick or pellet 14 to help hold and maintain the shape of the baked powder stick or pellet 14 during use (i.e., when the head section of the baked powder stick or pellet 14 experiences forces of being applied and rubbed along a user's face or other area of skin).

In the embodiment of FIGS. 1-4, the baked powder stick or pellet 14 has a generally cylindrical-shaped body section 14a (having a generally circular cross-section taken perpendicular to the axis A). The baked powder stick or pellet 14 also has a tapered section 14b, a head section 14c and a distal end section 14d. The head section 14c has a maximum outer diameter that is less than the outer diameter of the body section 14a. The tapered section 14b is located between the body section 14a and the head section 14c and tapers from the wider diameter of the body section 14a to a smaller diameter of the head section 14c. In particular embodiments, the head section 14c has a rounded shape, forming a portion of a sphere or spheroid. In other embodiments, the head section 14c has other suitable shapes, including, but not limited to a conical or frustoconical shape, multi-facet shape, a tapered shape that continues the taper of the tapered section 14b, or the like.

The distal end section 14d of the baked powder stick or pellet 14 has a generally cylindrical-shaped body section 14a (having a generally circular cross-section taken perpendicular to the axis A), similar to the shape of the body section 14a, but having a smaller diameter than the body section 14a. In the embodiment in FIGS. 1-4, the shape of each of the sections 14a-d is symmetrical about the axis A.

In particular embodiments, the baked powder stick or pellet 14 has a bullet-like shape (resembling the shape of a bullet). In other embodiments, the baked powder stick or pellet 14 has other suitable three-dimensional shapes, including, but not limited to other generally round-cylindrical shapes, other generally cylindrical shapes with polygonal or non-circular, curved cross-sections (taken perpendicular to the axis A), or those or other shapes that are not symmetrical about the axis A.

The baked powder stick or pellet 14 is held at least partially within a hollow interior of the base portion 12a of the housing 12, and either extends partially outward from, or is moveable to a position to extend partially outward from, a first open end of the base portion 12a (the upper end in FIG. 1). In particular embodiments, the base portion 12a of the housing 12 contains a moving mechanism for holding the baked powder stick or pellet 14 and selectively moving the baked powder stick or pellet 14 in a direction along the axis A, outward from the open end of the base portion 12a, to extend the tip of the head section 14c of the baked powder stick or pellet 14 a selected distance from the first open end of the base portion 12a. In such embodiments, the moving mechanism is configured to selectively move the baked powder stick or pellet 14 within the first section of the base portion component $12a_1$ in response to a manual rotation (about the axis A) of the base portion component $12a_2$ relative to the base portion component $12a_1$.

In particular embodiments, rotation of the base portion component $12a_2$ in a first rotary direction about the axis A (one of counterclockwise or clockwise) causes the moving mechanism to move the baked powder stick or pellet 14 in first linear direction along the axis A, to extend or further extend the baked powder stick or pellet 14 from the first open end of the base portion component $12a_1$. In this manner, a user may manually rotate the base portion component $12a_2$ in a first direction (and in a controlled manner) to adjust the distance that the baked powder stick or pellet 14 extends from the base portion 12a of the housing 12 (in a controlled manner).

In certain embodiments, the moving mechanism is configured to allow movement of the baked powder stick or pellet 14 in only one direction (e.g., a direction to extend or further extend the baked powder stick or pellet 14 from the base portion 12a of the housing 12). By allowing movement in only one direction, to extend or further extend the baked powder stick or pellet 14, the user will be instructed to (and will learn by experience to) control the movement of the baked powder stick or pellet 14 in a manner to minimize or limit the distance that the baked powder stick or pellet 14 extends from the base portion 12a. As such embodiments do not allow movement in the retraction direction, the user will be motivated to extend only enough of the powder stick or pellet 14 as needed for a given cosmetic application. This can result in less waist of the baked powder stick or pellet 14 and can help protect the baked powder stick or pellet 14 from breakage or crumbling. However, in other embodiments, the moving mechanism is configured to also allow movement of the baked powder stick or pellet 14 in a second direction along the axis A (e.g., a direction to retract the baked powder stick or pellet 14 further into the base portion 12a of the housing 12).

Figure 3:
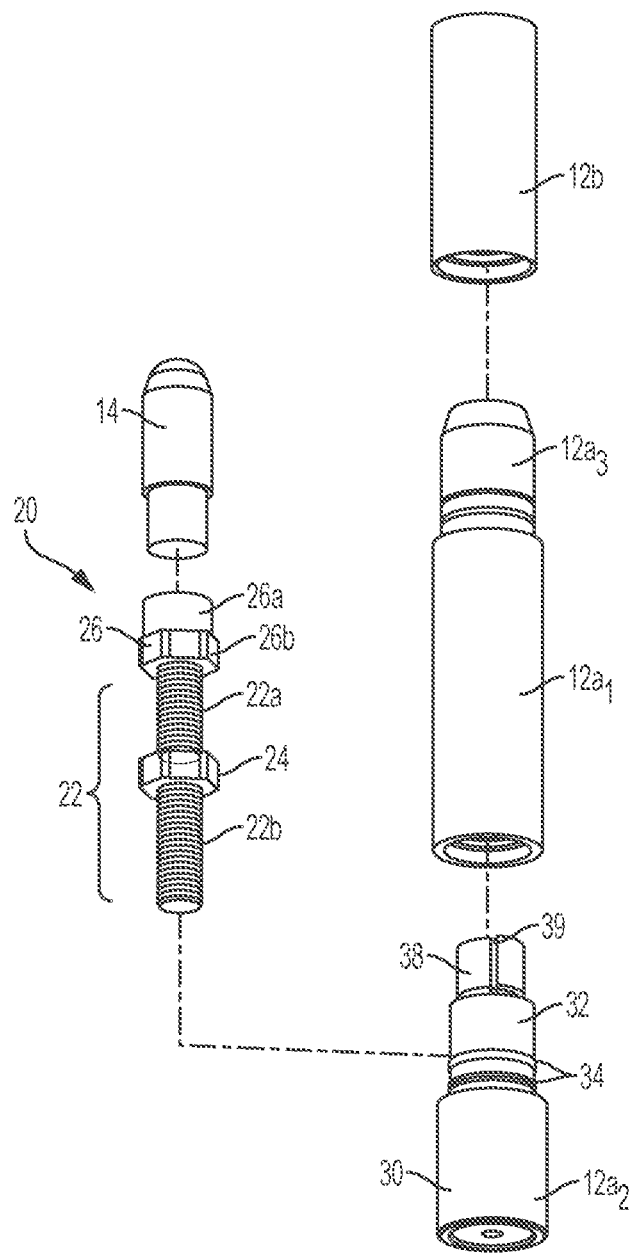
FIG. 3 is an exploded view of the baked powder pencil of FIG. 1.
Figure 4:
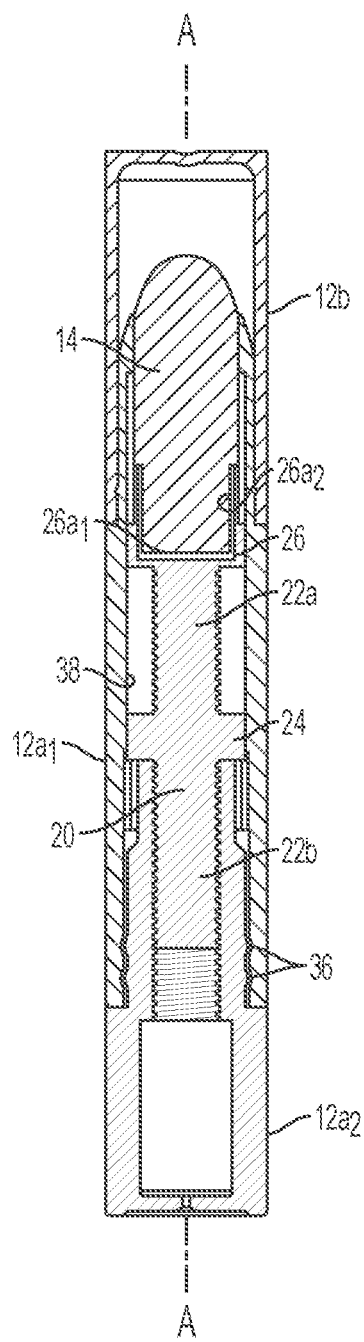
FIG. 4 is a cross-section view of the baked powder pencil of FIG. 1, where the cross-section is taken along the axis A.

With reference to FIGS. 3 and 4, an exploded view and a cross-section view of the baked powder pencil 10, including a moving mechanism 20, is shown. In the embodiment of FIGS. 3 and 4, the moving mechanism 20 includes a shaft 22 having a length dimension, with a first threaded section 22a and a second threaded section 22b along the length dimension. A nut or other protruding member 24 is provided in a central location along the length dimension of the shaft 22, separating the first threaded section 22a from the second threaded section 22b.

In particular embodiments, the nut or other protruding member 24 is formed integral with the threaded portions of the shaft 22, in a fixed location along the length dimension of the shaft 22. In other embodiments, the nut or protruding member 24 is a separate element relative to the shaft 22, and is threaded onto or otherwise secured to the shaft 22 at a fixed location along the length dimension of the shaft 22. In the illustrated embodiment, the nut or protruding member 24 is located at the center of the length dimension of the shaft 22, such that the first threaded section 22a has a length dimension that is approximately equal to the length dimension of the second threaded section 22b. In other embodiments, the length of the first threaded section 22a is greater than the length of the second threaded section 22b. In yet other embodiments, the length of the first threaded section 22a is less than the length of the second threaded section 22b. In further embodiments, the threads on the first section 22a may be omitted, such that the first section 22a has an unthreaded (or smooth) outer surface.

In particular embodiments, the nut or protruding member 24 has an outer surface that has a hexagonal cross-section shape (taken perpendicular to the lengthwise axis of the shaft 22) to inhibit rotation of the shaft 22 within the base portion component $12a_1$ of the housing 12, as described below. In other embodiments, the outer surface of the nut or protruding member 24 may have other suitable shapes that inhibit rotation, such as, but not limited to other polygonal shapes or non-circular, closed curve shapes (in cross-section taken perpendicular to the lengthwise axis of the shaft 22).

The moving mechanism 20 also includes a support structure 26 that supports the baked powder stick or pellet 14. In the illustrated embodiment, the support structure 26 includes a receptacle portion 26a that is configured to receive and contain at least a portion of the distal end section 14d of the baked powder stick or pellet 14. In the illustrated embodiment, the receptacle portion 26a has a cup shape including a bottom wall $26a_1$ and an annular side wall $26a_2$. In other embodiments, the receptacle portion has other suitable shapes including, but not limited to a flat plate shape. The support structure 26 also includes a second nut or protruding member 26b that has a suitable configuration for inhibiting rotation of the moving mechanism 20 within the base portion 12a, as described above with respect to nut or protruding member 24.

The moving mechanism 20 may be made of any suitable material or combination of materials having sufficient rigidity to operate as described herein, where such material may include, but is not limited to plastic, metal, ceramic, composite material, wood, or any combination thereof. In particular embodiments, the moving mechanism 20 (including the shaft portions 22a and 22b, the nut or protruding member 24 and the support structure 26 is formed as a single, unitary structure, for example, molded, formed in a 3D modeling system, or machined. In other embodiments, some or all of the shaft portions 22a and 22b, the nut or protruding member 24 and the support structure 26 are separate elements that are connected together in a fixed relation to each other.

As shown in FIG. 4 the moving mechanism 20 is configured to threadingly engage the base portion component $12a_2$. The base portion component $12a_2$ is configured to connect with the base portion component $12a_1$ in a rotary manner, such that the base portion component $12a_2$ can be manually rotated (about the axis A) relative to the base portion component $12a_1$.

In the embodiment of FIGS. 3 and 4, the base portion component $12a_2$ has a generally cylindrical first diameter section 30 that has an outer diameter that is approximately the same as the outer diameter of the base portion component $12a_2$. In addition, the base portion component $12a_2$ has a second diameter section 32 with a smaller outer diameter than the first diameter section 30. The second diameter section 32 extends from the first diameter section 30, in the direction of the axis A. The second diameter section 32 has an outer diameter size and shape suitable to fit within a second open end of the base portion section $12a_1$ (the bottom end of the base portion section $12a_1$ in FIGS. 1, 3 and 4).

One or more annular ribs 34 (two are shown in FIGS. 3 and 4) are provided around the outer surface of the second diameter section 32 (and around the axis A) of the base portion component $12a_2$. The annular ribs 34 are configured and arranged to fit within corresponding annular grooves 36 formed in the inner surface of the base portion component $12a_1$, near the second open end of the base portion component $12a_1$.

The annular ribs 34 and grooves 36 provide a mechanism for connecting the base portion component $12a_2$ to the base portion component $12a_2$, yet allow rotation of the base portion component $12a_2$ relative to the base portion component $12a_1$. In other embodiments other suitable mechanisms may be employed for connecting the base portion component $12a_2$ to the base portion component $12a_2$, and allow rotation of the base portion component $12b_2$ relative to the base portion component $12a_1$. In other embodiments the relative positions of the ribs and grooves are reversed such that the one or more ribs are on the inner surface of the base portion component $12a_1$, while the one or more grooves are on the second diameter section 32.

Figure 5:
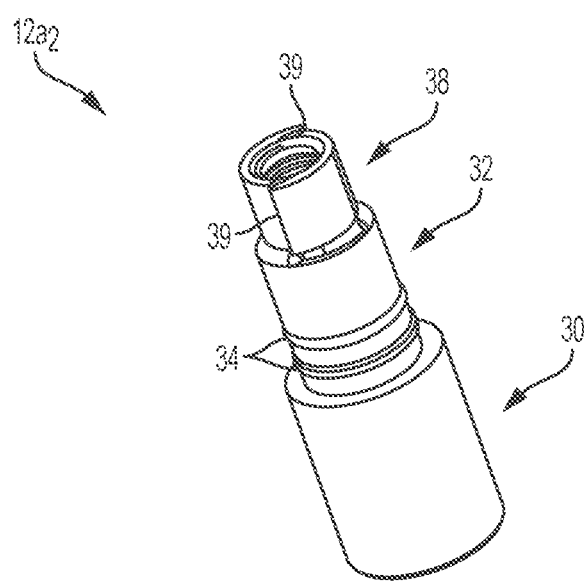
FIG. 5 is a perspective view of a base portion component of the baked powder pencil of FIG. 1.

In the embodiment of FIGS. 3 and 4, the base portion component $12a_2$ has a third diameter section 38, having a smaller outer diameter than the outer diameter of the second diameter section 34. In particular embodiments, the third diameter section 38 includes ratchet teeth 39 or other engagement surfaces that engage corresponding features on the inner surface of the base portion component $12a_1$, to inhibit rotation about the axis A of the base portion component $12a_2$ relative to the base portion component $12a_1$ in one direction (e.g., a clockwise direction), but allows relative rotation in the other direction (e.g., a counterclockwise direction). A further perspective view of the base portion component $12a_2$ and associated ratchet teeth 39 is shown in FIG. 5. In other embodiments, such ratchet teeth or other engagement features are omitted, allowing relative rotation in both directions. In yet other embodiments the relative positions of the ratchet teeth and engagement features are reversed such that the ratchet teeth are on the inner surface of the base portion component $12a_1$, while the further engagement features are on the third diameter section 38.

The third diameter section 38 and at least a portion of the second diameter section 32 form a hollow, cylindrical interior volume that is open on one end (the free end of the third diameter section 38) for receiving at least a portion of the shaft section 22b of the moving mechanism 20. The inner surface of the hollow interior formed by the third and second diameter sections 38 and 32 is threaded to match (and threadingly engage) the threads on the shaft section 22b of the moving mechanism 20.

As shown in FIG. 4, the shaft section 22b is engaged (in a screw threaded manner) with the base portion component $12a_2$. At the same time, the outer surface of the nut or protruding member 24 and the outer surface of the second nut or protruding member 26b are arranged to abut an inner surface 38 of the base portion component $12a_1$. In particular embodiments, the an inner surface 38 of the base portion component $12a_1$ is configured to match or engage with nuts or protruding members 24 and 26b in a manner that inhibits relative rotation of the moving mechanism 20 relative to the base portion component $12a_1$ of the housing 12.

Accordingly, when the base portion component $12a_2$ is rotated (about the axis A) relative to the base portion component $12a_1$ in one direction (e.g., a counterclockwise direction), the moving mechanism 20 is inhibited from rotating relative to the base portion component $12a_2$, and, thus, is moved linearly in the direction of axis A (due to the threaded interface between the moving mechanism 20 and the base portion component $12a_2$. In particular embodiments, the threads on the interface between the moving mechanism 20 and the base portion component $12a_2$ are configured such that rotation of the base portion component $12a_2$ about the axis A in a first direction (e.g., counterclockwise) causes the moving mechanism 20 to move in a direction to extend the baked powder stick or pellet 14 outward from or further outward from the first open end of the base portion component $12a_1$. As discussed above, further embodiments are configured such that rotation of the base portion component $12a_2$ about the axis A in a second direction (e.g., clockwise) causes the moving mechanism 20 to move in a direction to retract the baked powder stick or pellet 14 inward through the first open end of the base portion component $12a_1$.

The base portion component $12a_1$ is configured with one or more retention features to help retain the baked powder stick or pellet 14. In particular embodiments, such features are configured to allow the baked powder stick or pellet 14 to be moved in an extending direction (to extend or further extend the baked powder stick or pellet 14 from the first open end of the base portion component $12a_1$), but inhibits movement of the baked powder stick or pellet 14 in a retracting direction.

Figure 6:
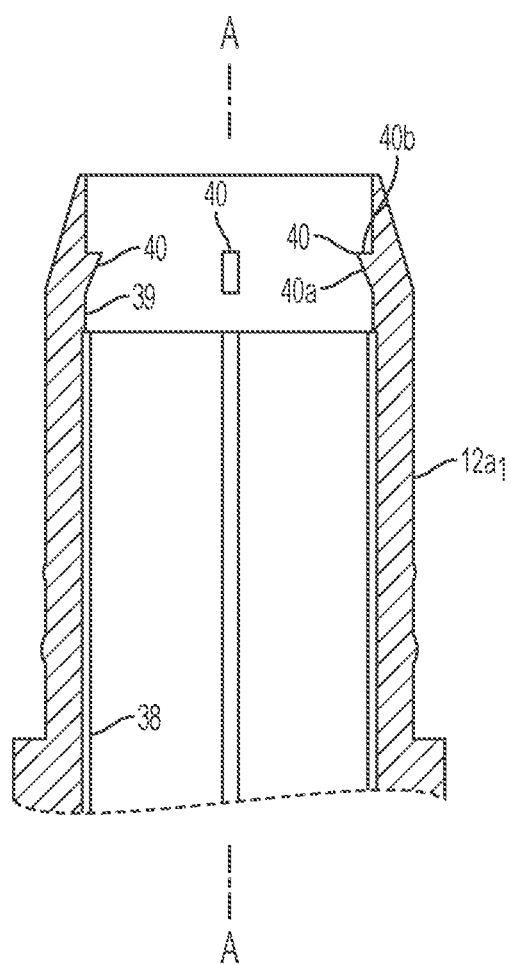
FIG. 6 is a partial cross-section view of a base portion component of the baked powder pencil of FIG. 1.
Figure 7:
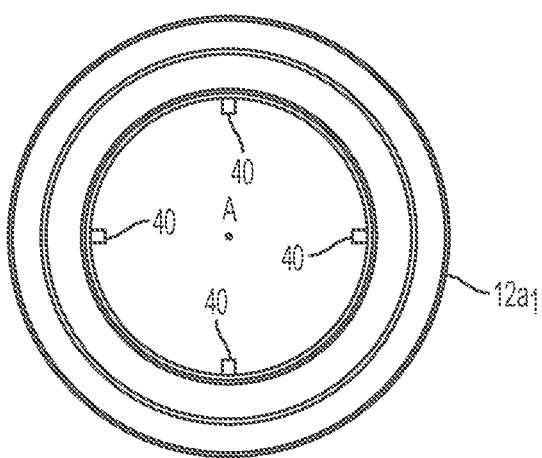
FIG. 7 is an end view of the base portion component of FIG. 6.

In the embodiment of FIGS. 6 and 7, the retention features include one or more (or a plurality of) projections 40 extending inward (toward the axis A) from an inner surface 39 (located above inner surface 38 in the orientation of FIG. 7) of the base portion component $12a_1$. The projections 40 are arranged near, but spaced inward from the first open end of the base portion component $12a_1$. In other embodiments, the projections are arranged at the edge of the opening on the open end of the base portion component $12a_1$. In the illustrated embodiment, four projections 40 are arranged at equally spaced intervals, around the axis A. In other embodiments more or less than four projections 40 are employed. In particular embodiments, the projections 40 are formed integral with the base portion component $12a_1$, for example, but not limited to, being molded with the base portion component $12a_1$. In other embodiments, the projections 40 are separate elements that are attached in a fixed position to the base portion component $12a_1$.

In particular embodiments, each projection 40 has a relatively thin, ramp shape that forms a tapered surface 40a facing inward, into the base portion component 12$a_1$, and a second surface 40b facing toward the open end of the base portion component 12$a_1$. The first surface 40a is tapered, inclined or angled (at an oblique angle) relative to the axis A. The second surface 40b is generally perpendicular to the axis A. The projections 40 are configured to engage the outer surface of the body section 14a of the baked powder stick or pellet 14. In particular, as the baked powder stick or pellet 14 is moved (by the moving mechanism 20) in the extending direction (i.e., upward in the direction of FIGS. 1 and 6), the ramp shape of the projections allows the projections to cut slightly into the outer surface of the body section 14a. In this manner, the projections 40 extend into the body section 14a and help to retain the baked powder stick or pellet 14 within the base portion component 12$a_1$ of the housing 12 (and inhibit accidental removal or dropping of the baked powder stick or pellet 14 out of the base portion component 12$a_1$ of the housing 12). While the tapered surface 40a of each ramp-shaped projection 40 allows the baked powder stick or pellet 14 to be moved in the extending direction (i.e., upward in the direction of FIGS. 1 and 6), the perpendicular surface 40b of the projections 40 inhibits movement of the baked powder stick or pellet 14 in a retraction direction (i.e., downward in the direction of FIGS. 1 and 6).

In the embodiment of FIGS. 1-7, the baked powder stick or pellet 14 has a rounded (or partially spherical or spheroidal) head portion 14c that protrudes outward (e.g., outward from the open end of the base portion component 12$a_1$ by a sufficient amount to allow a user to directly apply the head portion 14c to the user's skin. Thus, a user may hold the housing base 12a in one hand and contact a desired part of the user's face (or other area of skin) with the protruding head portion 14c, to apply baked powder to the user's face (or other area of skin). In particular embodiments, the head portion 14c of the baked powder stick or pellet 14 is configured in a shape that enhances the ability to apply the baked powder in a precise or controlled manner.

Figure 8:
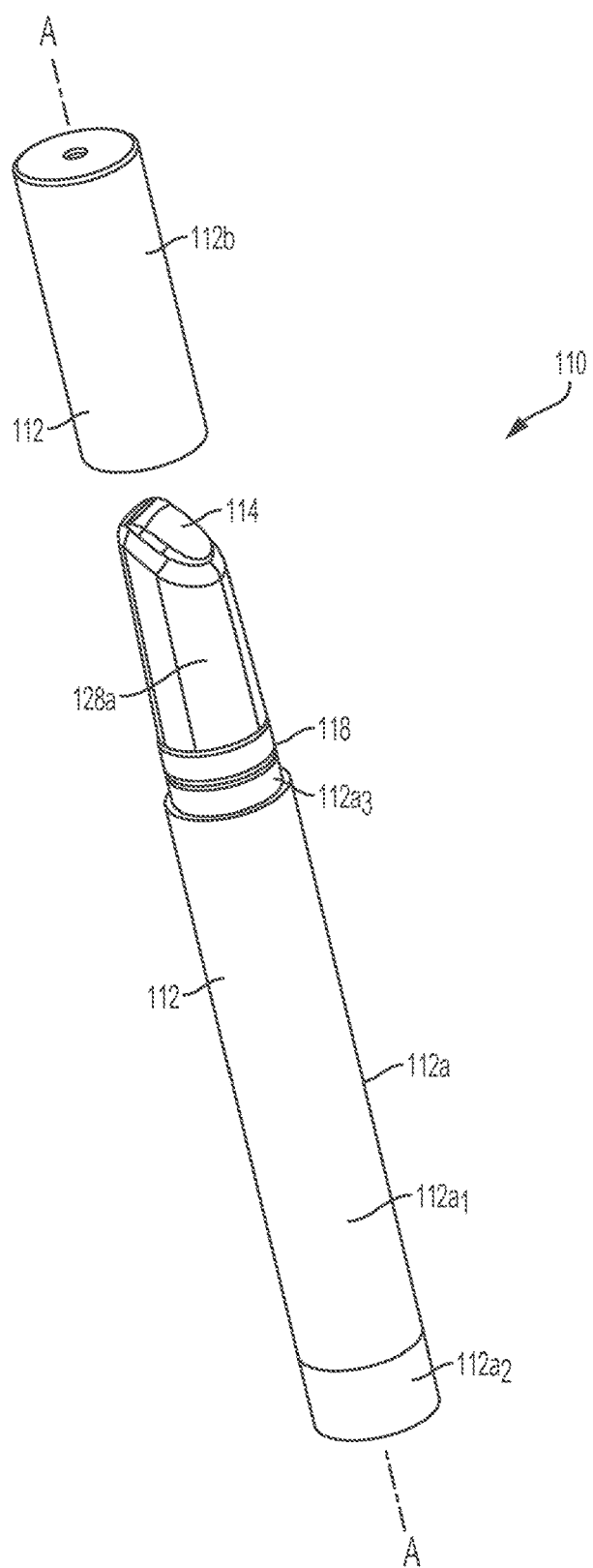
FIG. 8 is a perspective view of a baked powder pencil according to a further embodiment.

For example, a baked powder pencil 110 according to a further embodiment is shown in FIGS. 8-15, where the baked powder pencil 110 has a baked powder stick or pellet 114 that has a shape configured to provide multiple contact surfaces of different widths, lengths or shapes, to provide different effects when applied to the user's face (or other area of skin). The baked powder stick or pellet 114 is made of a material and by a process similar to any of the example materials and processes described above with respect to baked powder stick or pellet 14, but is shaped as described herein. A perspective view of the baked powder pencil 110, with the cap portion removed from the base portion of the housing is shown in FIG. 8. FIGS. 9-15 show various views of the baked powder stick or pellet 114, including a perspective view in FIG. 9, right and left side views in FIGS. 10 and 11, back and front views in FIGS. 12 and 13 and top and bottom views in FIGS. 14 and 15.

With reference to FIGS. 9-15, the baked powder stick or pellet 114 has a generally longitudinal shape that has a lengthwise dimension along an axis A. The baked powder stick or pellet 114 has a semi-cylindrical or curved front surface 114a extending lengthwise in the direction of the axis A and curved partially around the axis A. The baked powder stick or pellet 114 has a generally flat or planar back surface 114b extending lengthwise in the direction of the axis A and widthwise in a direction perpendicular to the axis A. In particular embodiments, generally flat or planar side surfaces 114c and 114d extend widthwise from the front surface 114a to the back surface 114b, and lengthwise in the direction of the axis A. In other embodiments, the semi-cylindrical or curved front surface 114a extends all of the way to the rear surface 114b, instead of the flat or planar side surfaces 114c and 114b.

In the embodiment of FIGS. 8-15, the baked powder stick or pellet 114 has a head section 114e that is shaped with multiple, generally planar surfaces extending in multiple respectively different planes. In particular embodiments, the multiple different planes extend at multiple different respective angles (e.g., oblique angles) relative to each other and relative to the axis A. In the illustrated embodiment, the head section 114e has two surfaces (generally planar first and second surfaces 114$e_1$ and 114$e_2$) in two different planes. In other embodiments, the head section is formed with three surfaces in three different planes (or more than three surfaces in more than three different planes). The generally planar first surface 114$e_1$ extends in a first plane that is inclined or angled (at an oblique angle) relative to the axis A. The generally planar first surface 114$e_1$ extends from the semi-cylindrical or curved front surface 114a, toward the generally planar back surface 114b, and from one side surface 114c to the other side surface 114d.

In particular embodiments, the angle of the first plane (the plane of the first surface 1140 relative to the axis A is between about 20 and 80 degrees. In other embodiments, that angle is between 30 and 60 degrees. In particular embodiments, that angle is about 45 degrees. In other embodiments, the angle of the first plane relative to the axis A is any other suitable oblique angle.

The generally planar second surface 114$e_2$ extends between the first surface 114$e_1$ and the back surface 114b, and from one side surface 114c to the other side surface 114d. The second surface 114$e_2$ is generally flat and extends in a second plane that is neither the same as, nor parallel to, the first plane in which the first surface 114$e_1$ extends. Accordingly, as shown in FIGS. 8-15, the second surface 114$e_2$ is angled at an oblique angle relative to the first surface 114$e_1$. In particular embodiments, the second surface 114$e_2$ has a generally flat or planar shape. In other embodiments, the second surface 114$e_2$ has other shapes such as, but not limited to an outwardly bowed or projecting shape, a generally semi-cylindrical shape, a rounded semi-spherical or semi-spheroidal shape, or the like.

The multiple surfaces of the head section 114e of the baked powder stick or pellet 114 provide a user with multiple options for applying the baked powder cosmetic to the user's face (or other skin area). For example, the first surface 114$e_1$ has a relatively large surface area (as compared to the second surface 114$e_2$) and, thus, can apply a relatively wide band, spot or patch of baked powder cosmetic on the user's face (or other skin area), when the first surface 114$e_1$ is applied (e.g., contacted with and wiped or dabbed on the face or other skin area). Accordingly, with the first surface 114$e_1$, a user may draw a relatively wide line or pattern (as compared to the second surface 114$e_2$). Furthermore, the curved front edge of the first surface 114$e_1$ (provided by virtue of the shape of the semi-cylindrical or curved front surface 114a) enhances the ability of the user to control the width of the line or pattern drawn to be about the width defined by the widest portion of the first surface 114$e_1$ (i.e., the portion of the first surface 114$e_1$ closest to the back surface 114b). In addition, the oblique angle of the first surface 114$e_1$ relative to the second surface 114$e_2$, allows the user to apply the first surface 114$e_1$ to the skin, while the second surface 114$e_2$ is separated from the skin (for example, by contacting the skin with the first surface $114e_1$ lying generally flat or parallel to the surface of the skin).

The second surface $114e_2$ has a smaller surface area than the first surface $114e_1$. The second surface $114e_2$ has a first width dimension (from one side surface $114c$ to the other side surface $114d$) that is about the same width as the widest portion of the first surface $114e_1$. However, the second surface $114e_2$ has a second width dimension (from the first surface $114e_1$ to the back surface $114b$, that is smaller (narrower) than the same width dimension of the first surface $114e_1$ (from the front surface $114a$ to the second surface $114e_2$). Accordingly, the second surface $114e_2$ provides a relatively narrow surface area (in a side dimension as shown in the side views of FIGS. 9 and 10) that allows the user to draw a relatively thin line or pattern (as compared to the first surface $114e_1$). In addition, the oblique angle of the first surface $114e_1$ relative to the second surface $114e_2$, allows the user to apply the second surface $114e_2$ to the skin, while the first surface $114e_1$ is separated from the skin (for example, by contacting the skin with the second surface $114e_2$ lying generally flat or parallel to the surface of the skin).

The baked powder pencil 110 (FIG. 8) includes a housing 112 that holds the baked powder stick or pellet 14. The housing 112 includes a base portion 112a and a cap portion 112b. The base portion 112a of the housing 112 has two components $112a_1$ and $112a_2$, where the base portion component and $112a_2$ is connected to the base portion component $112a_1$ for rotation about the axis A relative to the base portion component and $112a_1$. The base portion component $112a_1$ includes a reduced diameter portion $112a_3$, on which one or more raised members 118 are provided (similar in structure and operation as the reduced diameter portion $12a_3$ and raised members 18 described above with respect to FIGS. 1-7).

The housing 112 is shown in FIG. 8, with the cap portion 112b removed from the base portion 112a. In particular embodiments, the housing 112 (and the baked powder stick or pellet 114) has a smaller cross-section diameter (taken perpendicular to the axis A) than the housing 12 in FIG. 1. In such embodiments, the baked powder pencil 110 in FIG. 8 has a relatively thin or small-diameter form factor as compared to the baked powder pencil in FIG. 1. In such embodiments, a user can apply thinner or finer lines or patterns of baked powder to the user's face (or other skin area), as compared to the larger diameter baked powder pencil in FIG. 1. In other embodiments, the baked powder pencil 110 in FIG. 8 has a cross-section diameter that is about the same as, or larger than, the cross-section diameter of the baked powder pencil 10 in FIG. 1.

The baked powder stick or pellet 114 is held by the base portion 112a of the housing 112, with at least a portion of the baked powder stick or pellet 114 extending out from one end of the housing 112. In particular embodiments, the base portion 112a of the housing 112 contains components for retaining the baked powder stick or pellet 114 and, in some embodiments, for selectively increasing (or decreasing, or both) the distance that the baked powder stick or pellet 114 extends from the base portion 112a of the housing 112.

The baked powder stick or pellet 114 is held at least partially within a hollow interior of the base portion 112a of the housing 112, and either extends partially outward from or is moveable to a position to extend partially outward from a first open end of the base portion 112a (the upper end in FIG. 8). In particular embodiments, the base portion 112a of the housing 112 contains a moving mechanism for holding the baked powder stick or pellet 114 and selectively moving the baked powder stick or pellet 114 in a direction along the axis A, outward from the open end of the base portion 112a, to extend the tip of the head section 114e of the baked powder stick or pellet 114 a selected distance from the first open end of the base portion 112a. In such embodiments, the moving mechanism is configured to selectively move the baked powder stick or pellet 114 within the first base portion component $112a_1$ in response to a manual rotation (about the axis A) of the second base portion component $112a_2$ relative to the base portion component $112a_1$.

In particular embodiments, the moving mechanism in the base portion 112a of the housing 112 is similar to the moving mechanism described above with respect to FIGS. 1-7. In such embodiments, the base portion 112a (including components $112a_1$ and $112a_2$) and the cap 112b are similar to the base portion 12a (including components $12a_1$ and $12a_2$) and the cap 12b described above with respect to FIGS. 1-7. Accordingly, for such embodiments, the description above relating to the moving mechanism 20, the base portion 12a (including components $12a_1$ and $12a_2$) and the cap 12b are incorporated herein by reference.

In other embodiments, the moving mechanism, base portion or cap in the embodiment of FIG. 8 is different from the moving mechanism, base portion or cap of FIGS. 1-7. For example, in other embodiments, the moving mechanism in the base portion 112a of FIG. 8 has a configuration as described and shown with respect to FIGS. 16 and 17.

Figure 16:
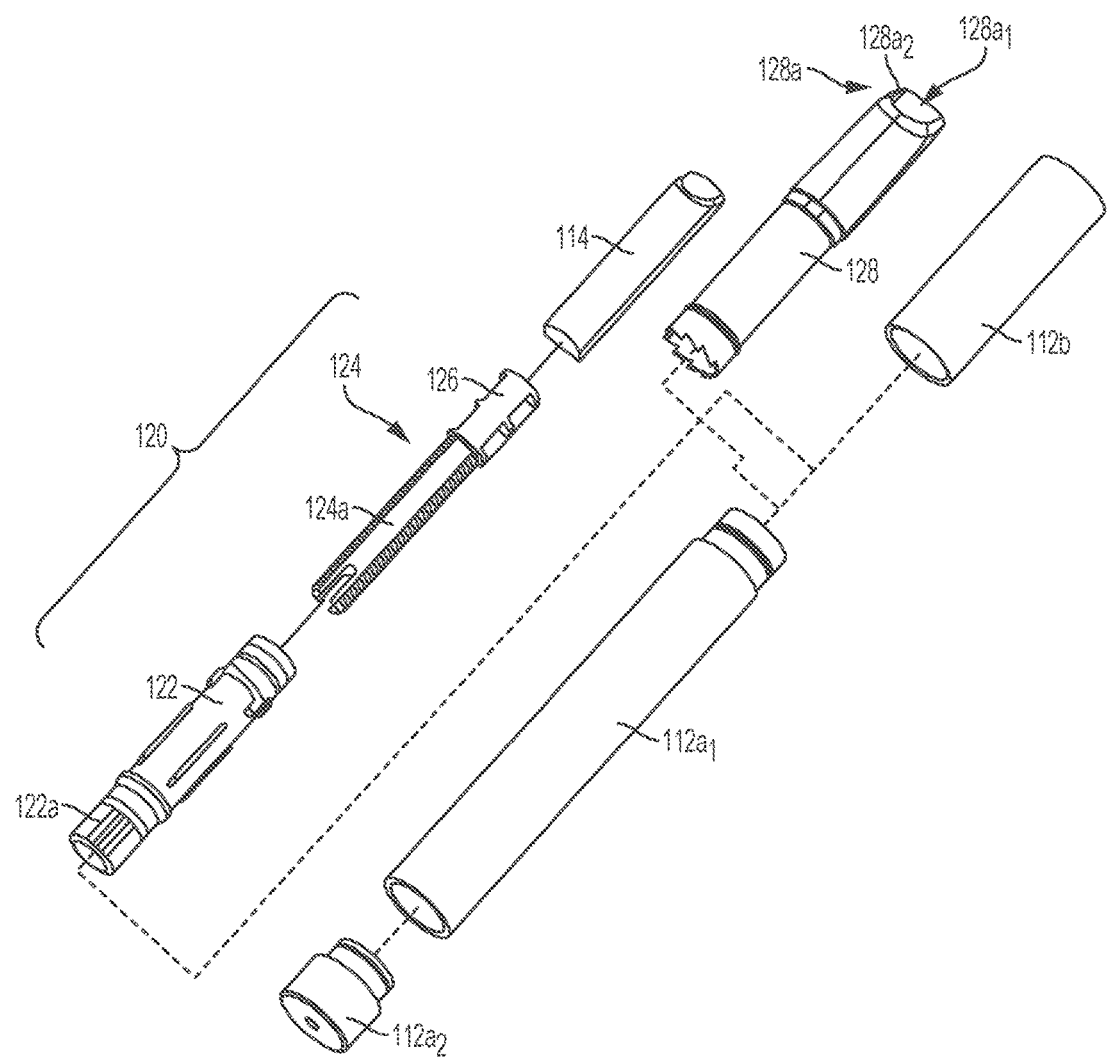
FIG. 16 is an exploded view of the baked powder pencil of FIG. 8.
Figure 17:
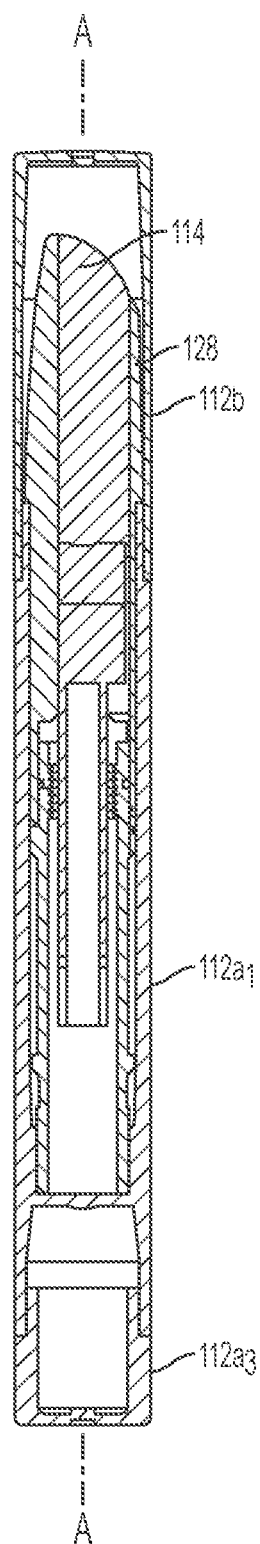
FIG. 17 is a cross-section view of the baked powder pencil of FIG. 8, where the cross-section is taken along the axis A.

In the embodiment of FIGS. 16 and 17, a moving mechanism 120 includes a tube member 122 and a support structure 124. In addition, the embodiment of FIGS. 8, 16 and 17 includes a guide member 128. The tube member 122 has a generally cylindrical shape with a hollow, generally cylindrical interior. One end 122a of the tube member 122 has a set of knurls or gear teeth configured to engage and mate with a corresponding set of knurls or teeth on the inner surface of a hollow interior of the base portion component $112a_2$. In other embodiments, the tube member 122 is formed integral with the base portion component $112a_2$, as a single, unitary structure. Accordingly, the tube member 122 rotates about the axis A, relative to the base portion component $112a_1$, when the base portion component $112a_2$ is manually rotated about the axis A relative to the base portion component $112a_1$. The inner surface of the hollow interior of the tube member 122 is threaded.

The support structure 124 has a shaft portion 124a that has a lengthwise dimension extending in the direction of axis A. The shaft portion 124a has an outer surface provided with threads that match (or mate with) the threads on the inner surface of the tube member 122. The support structure 124 also includes a receptacle portion 126 for holding or abutting against an end portion of the baked powder stick or pellet 114.

The guide member 128 has a generally cylindrical tube shape, with a hollow, generally cylindrical interior. The guide member 128 is configured to receive a length portion of the baked powder stick or pellet 114 and the receptacle portion 126 within the hollow interior of the guide member. The inner wall surface of the hollow guide member 128 surrounds a length portion of the baked powder stick or pellet 114, to help support the baked powder stick or pellet 114 during use, and help retain the shape of the baked powder stick or pellet 114.

An end portion 128a of the guide member 128 has an opening $128a_1$ through which a portion of the baked powder stick or pellet 114 extends. The end portion 128a of the guide member 128 has an annular edge $128a_2$ that surrounds the opening $128a_1$. The annular edge is inclined or angled relative to the axis A (extends in a plane that is at an oblique angle relative to the axis A). In particular embodiments, the angle of the annular edge $128a_2$ relative to the axis A is about the same (matches) the oblique angle of the head section $114a$ of the baked powder stick or pellet 114, when the baked powder stick or pellet 114 is received within the hollow interior of the guide member 128.

The head section $114e$ includes a generally planar first surface $114e_1$ extending in a first plane that is inclined or angled (at an oblique angle) relative to the axis A. Accordingly, only a small portion of the shaped end section $114e$ of the baked powder stick or pellet 114 needs to extend outward from the opening $128a_1$ to be exposed for use. The shape of the end portion $128a$ and the angle of the annular edge $128a_2$ of the guide member 128 is such that the end portion $128a$ and annular edge $128a_2$ of the guide member 128 surrounds the head section $114e$ of the baked powder stick or pellet 114 and follows the contour of the multiple surfaces of the head section $114e$. In that manner, the multiple surfaces of the head section $114e$ can be exposed and used in the manner discussed above, while the guide member 128 supports the baked powder stick or pellet 114 and helps retain the shape of head section $114e$ of the baked powder stick or pellet 114.

The moving mechanism 120 is configured to selectively move the baked powder stick or pellet 114 within the guide member 128 and base portion component $112a_1$ in response to a manual rotation (about the axis A) of the base portion component $112a_2$ relative to the base portion component $112a_1$. In particular embodiments, rotation of the base portion component $112a_2$ in a first rotary direction about the axis A (one of counterclockwise or clockwise) causes the moving mechanism 120 to move the baked powder stick or pellet 114 in first linear direction along the axis A, to extend or further extend the baked powder stick or pellet 114 through the opening $128a_1$ of the guide member 128. In this manner, a user may manually rotate the base portion component $112a_2$ in a first direction to adjust the distance that the baked powder stick or pellet 114 extends from the guide member 128 (and, thus, from the base portion $112a$ of the housing 112).

In certain embodiments, the moving mechanism 120 is configured to allow movement of the baked powder stick or pellet 114 in only one direction (e.g., a direction to further extend the baked powder stick or pellet 114 from the base portion $112a$ of the housing 112). In other embodiments, the moving mechanism is configured to also allow movement of the baked powder stick or pellet 114 in a second direction along the axis A (e.g., a direction to retract the baked powder stick or pellet 114 further into the base portion $112a$ of the housing 112).

More specifically, manual rotation of the base portion component $112a_2$ about the axis A relative to the base portion component $112a_1$ causes the tube member 122 to rotate about the axis A. Rotation of the tube member 122 causes a linear movement of the support structure 124 in the direction of the axis A, resulting in linear movement of the baked powder stick or pellet 114 in the direction of the axis A. In this manner, a user may manually rotate the base portion component $112a_2$ in a first direction to adjust the distance that the baked powder stick or pellet 114 extends from the base portion $112a$ of the housing 112. In particular embodiments, one end portion (the lower end portion in FIG. 16) of the guide member 128 has a set of ratchet teeth that are configured to engage one or more ratchet teeth or stop surfaces on the tube member 122, to allow rotation of the tube member 122 in one direction (e.g., a direction for extending or further extending the baked powder stick or pellet 114 from the opening $128a_1$ of the guide member 128), but inhibits rotation in the opposite direct (e.g., a retraction direction). In such embodiments, the guide member 128 has an outer surface (having a non-circular cross-section shape) that is configured to engage a correspondingly shaped inner surface of the base portion component $112a_1$, where the engaged surfaces inhibit rotation of the guide member 128 relative to the base portion component $112a_1$.

In particular embodiments, the inner surface of the guide member 128 includes one or more (or a plurality of) projections, such as the ramp-shaped projections 40 described above with respect to the embodiment of FIG. 1-7. In other embodiments, the guide member 128 does not include projections 40 and, instead, has a length and diameter suitable for retaining the baked powder stick or pellet 114.

Figure 18:
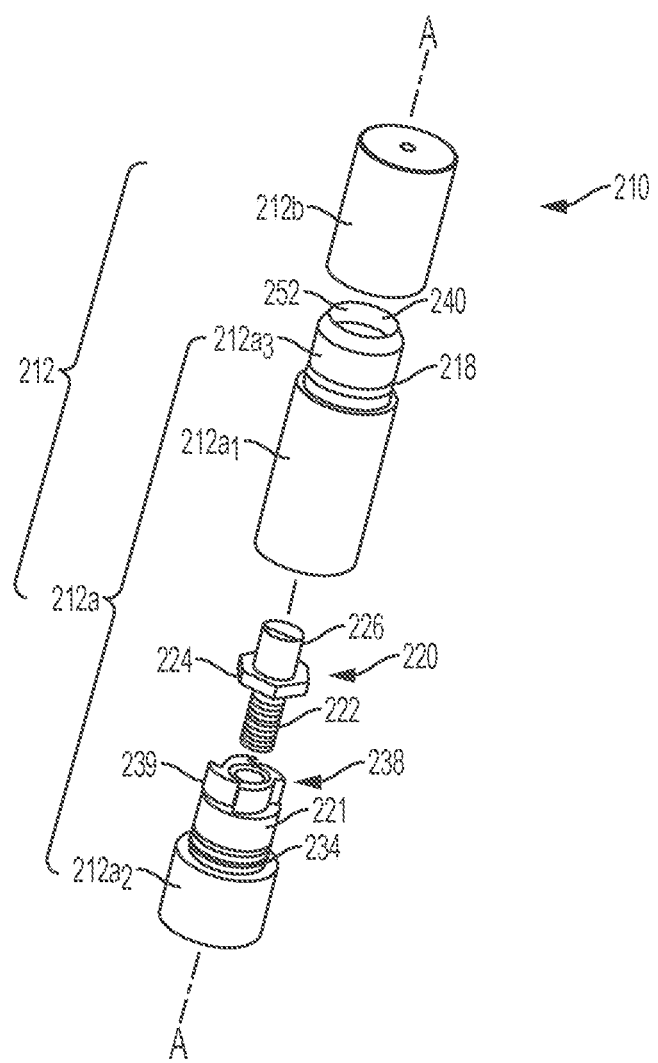
FIG. 18 is an exploded view of a baked powder pencil according to a further embodiment.
Figure 19:
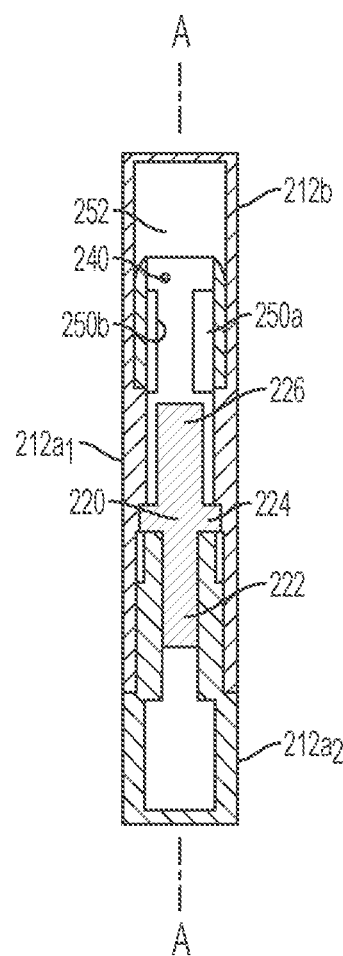
FIG. 19 is a cross-section view of the baked powder pencil of FIG. 18.

A baked powder pencil 210 according to a further embodiment is shown in FIGS. 18-21. An exploded, perspective view of the baked powder pencil 210 is shown in FIG. 18. A cross-sectional view of the baked powder pencil 210, is shown in FIG. 19. In particular embodiments, when assembled, the backed powder pencil 210 appears similar to the baked powder pencil 10 shown in FIG. 1 (and may have similar or different relative dimensions than the baked powder pencil 10 in FIG. 1).

The baked powder pencil 210 (FIG. 18) includes a housing 212 that holds the baked powder stick or pellet. The baked powder stick or pellet (not shown in FIGS. 18-20) may be similar to, or according to, any of the baked powder stick or pellet configurations described with respect to the embodiments of FIGS. 1-17, or may have other suitable configurations. The housing 212 includes a base portion $212a$ and a cap portion $212b$. The base portion $212a$ of the housing 212 has two components $212a1$ and $212a2$, where the base portion component and $212a2$ is connected to the base portion component $212a1$ for rotation about the axis A relative to the base portion component and $212a1$. The base portion component $212a1$ includes a reduced diameter portion $212a3$, on which one or more raised members 218 are provided (similar in structure and operation as the reduced diameter portion $12a3$ and raised members 18 described above with respect to FIGS. 1-7).

The housing 212 is shown in FIG. 18, with the cap portion $212b$ removed from the base portion $212a$. In particular embodiments, the housing 212 (and the baked powder stick or pellet contained in that housing) has a smaller cross-section diameter (taken perpendicular to the axis A) than the housing 12 in FIG. 1. In such embodiments, the baked powder pencil 210 in FIG. 18 has a relatively thin or small-diameter form factor as compared to the baked powder pencil in FIG. 1. In such embodiments, a user can apply thinner or finer lines or patterns of baked powder to the user's face (or other skin area), as compared to the larger diameter baked powder pencil in FIG. 1. In other embodiments, the housing 212 of the baked powder pencil 210 in FIG. 18 has a cross-section diameter that is about the same as, or larger than, the cross-section diameter of the housing 12 of the baked powder pencil 10 in FIG. 1.

When the housing 212 is filled with (receives or contains) the baked powder stick or pellet, the baked powder stick or pellet is held within the base portion $212a$ of the housing 212, with at least a portion of the baked powder stick or pellet extending out from the cap end of the housing 212, for example, in a manner similar to, but not limited to a manner as described and shown with respect to the embodiments of FIGS. 1-17. In particular embodiments, the base portion $212a$ of the housing 212 contains components for retaining the baked powder stick or pellet and, in some embodiments, for selectively increasing (or decreasing, or both) the distance that the baked powder stick or pellet extends from the base portion 212a of the housing 212. In certain embodiments, such components are configured to contain or hold a portion of the baked powder stick or pellet. In other embodiments, such components may be configured to abut the baked powder stick or pencil, but do not contain any portion of the baked powder stick or pellet.

When installed and received in the housing 212, the baked powder stick or pellet is held at least partially within a hollow interior of the base portion 212a of the housing 212, and either extends partially outward from or is moveable to a position to extend partially outward from a first open end of the base portion 212a (the cap end or upper end in FIG. 18). In particular embodiments, the base portion 212a of the housing 212 contains a moving mechanism for selectively moving the baked powder stick or pellet in a direction along the axis A, outward from the first open end of the base portion 212a, to extend the tip of a head section of the baked powder stick or pellet a selected distance from the first open end of the base portion 212a. In such embodiments, the moving mechanism is configured to selectively move the baked powder stick or pellet within the first base portion component 212a1 in response to a manual rotation (about the axis A) of the second base portion component 212a2 relative to the base portion component 212a1.

In particular embodiments, the moving mechanism 220 in the base portion 212a of the housing 212 is similar to the moving mechanism 20 described above with respect to FIGS. 1-7. In such embodiments, the base portion 212a (including components 212a1 and 212a2) and the cap 212b are similar to the base portion 12a (including components 12a1 and 12a2) and the cap 12b described above with respect to FIGS. 1-7. Accordingly, for such embodiments, the description above relating to the moving mechanism 20, the base portion 12a (including components 12a1 and 12a2) and the cap 12b are incorporated herein by reference.

In other embodiments, the moving mechanism in the base portion 212a of the housing 212 is similar to the moving mechanism 120 described above with respect to FIGS. 16 and 17. In such embodiments, the base portion 212a (including components 212a1 and 212a2) and the cap 212b are similar to the base portion 112a (including components 112a1 and 112a2) and the cap 112b described above with respect to FIGS. 8-17. Accordingly, for such embodiments, the description above relating to the moving mechanism 120, the base portion 112a (including components 112a1 and 112a2) and the cap 112b are incorporated herein by reference. In other embodiments, the moving mechanism, base portion or cap in the embodiment of FIG. 18 is different from the moving mechanisms, base portions or caps of FIGS. 1-17.

In the embodiment of FIGS. 18-21, a moving mechanism 220 operates with a tube member 221. The tube member 221 has a generally cylindrical shape with a hollow, generally cylindrical interior. In certain embodiments, the tube member 221 may be formed integral with the base portion component 212a2. In other embodiments, the tube member 221 may be formed as a separate member relative to the base portion component 212a2, and is connected to the base portion component 212a2 in any suitable manner, such as, but not limited to engaging or mating sets of knurls or gear teeth on the outer surface of one end of the tube member 221 and on the inner surface of a hollow interior of the base portion component 212a2 (for example, similar to that on the embodiment in FIG. 16, at the end 122a of the tube member 122). Accordingly, the tube member 221 rotates about the axis A, relative to the base portion component 212a1, when the base portion component 212a2 is manually rotated about the axis A relative to the base portion component 212a1. An inner surface of the hollow interior of the tube member 221 is threaded.

The moving mechanism 220 has a shaft portion 222 that has a lengthwise dimension extending in the direction of axis A. The shaft portion 222 has an outer surface provided with threads that match (or mate with) the threads on the inner surface of the tube member 221. The moving mechanism 220 also includes a head portion 226. In particular embodiments, the head portion 226 is composed of an unthreaded, free end of the shaft 222. In other embodiments, the head portion 226 is configured as a ram or piston head that has a larger diameter (in a dimension perpendicular to the axis A) than the diameter of the shaft portion 222. In particular embodiments, the outer diameter of the head portion 226 matches (or is slightly smaller than) an inner diameter of the base portion component 212a1, to allow the support structure 224 to move linearly (in the direction of axis A) within the interior of the base portion component 212a1. In embodiments where the interior surface of the base portion component 212a1 has a hexagonal (or other non-circular) cross section shape (taken perpendicular to the axis A), the outer diameter of the head portion 226 matches (or is slightly smaller than) the inner diameter of the base portion component 212a1 as defined by the flat surface areas of the hexagonal shape (or by the smallest diameter portion of the non-circular shape). In such embodiments, the head portion 226 may help to stabilize the moving mechanism 220, and inhibit lateral motion (in a direction transverse to the axis A) of the moving mechanism 220 relative to the base portion component 212a1, as the moving mechanism 220 is moved in a linear direction along the axis A relative to the base portion component 212a1.

In certain embodiments, the head portion 226 may be provided with a cup shape configuration, for example, but not limited to, a cup shape receptacle portion as described with respect to receptacle portion 26a in the embodiment of FIGS. 1-7. Such embodiments can provide additional stability to minimize lateral motion (transverse to the axis A) of the baked powder stick or pellet within the base portion 212a and can help retain the baked powder stick or pellet within the base portion 212a.

However, in particular embodiments, the head portion 226 of the moving mechanism 220 has a generally flat surface at its free end (upper end in FIG. 18) for contacting and abutting against an end of the baked powder stick or pellet, while minimizing stress on the baked powder stick or pellet, when the baked powder stick or pellet is located within the base portion 212a. The generally flat surface has a surface area that extends generally transverse (for example, but not limited to, perpendicular) to the axis A and provides an abutment to push against one end of the baked powder stick or pellet, as the moving mechanism 220 moves linearly along the axis A, in a direction to further repel the baked powder stick or pellet from the open end (cap end) of the base portion 212a.

Thus, in particular embodiments, to minimize lateral sheer forces on the baked powder stick or pellet, the flat end surface of the head portion 226 has no (or minimal) cup shape feature and no (or minimal) other features that extend between the baked powder stick or pellet and a the surface of the inner wall of the base portion 212a. Such embodiments can provide additional flexibility regarding the type of baked powder stick or pellet that can be employed, for example, allowing for relatively fragile baked powder stick or pellet structures to retain their shape (without breaking apart inside of the base portion 212a) when moved in a linear direction of axis A within the base portion 212a. In embodiments in which the head portion 226 of the moving mechanism 220 has a generally flat configuration (or embodiments in which a cup-shaped or other suitable configuration is employed), additional lateral stability can be provided by stabilizing members described below.

In particular embodiments, the moving mechanism 220 includes one or more nuts or other protruding members 224 is provided in a central location along the length dimension of the shaft 222. The nut or other protruding member 224 may be similar in structure and operation to the nut or other protruding member 24 described above with respect to the embodiment of FIGS. 1-7.

In particular embodiments, the nut or protruding member 224 has an outer surface that has a hexagonal cross-section shape (taken perpendicular to the lengthwise axis of the shaft 222) that matches or mates with a correspondingly shaped inner surface of the base portion component 212a1, to inhibit rotation of the shaft 222 relative to the base portion component 212a1, as described below. In the example shown in FIGS. 20 and 21, the inner surface of the base portion component 212a1 has a generally hexagonal cross-section shape, to correspond to a generally hexagonal shaped nut or protruding member 224. In other embodiments, the outer surface of the nut or protruding member 224 may have other suitable shapes that inhibit rotation, such as, but not limited to other polygonal shapes or non-circular, closed curve shapes (in cross-section taken perpendicular to the lengthwise axis A of the shaft 222).

In certain embodiments, the moving mechanism 220 also includes a second nut or protruding member (for example, but not limited to, a nut or protruding member similar to 26b in the embodiment of FIGS. 1-7) that has a suitable configuration for inhibiting rotation of the moving mechanism 220 relative to the base portion component 212a1. The first and second nuts and/or protruding members (or one of such members, when the other is omitted) are/is configured to mate with a correspondingly shaped interior surface of the base portion component 212a1, to allow linear movement of the moving mechanism 220 within the base portion component 212a1, but inhibit rotation of the moving mechanism 220 about the axis A, relative to the base portion component 212a1.

The moving mechanism 220 may be made of any one or more suitable materials or combination of materials having sufficient rigidity to operate as described herein, where such material may include, but is not limited to plastic, metal, ceramic, composite material, wood, or any combination thereof. In particular embodiments, the moving mechanism 220 (including the shaft 222, the nut or protruding member 224 and the head portion 226 is formed as a single, unitary structure, for example, molded, formed in a 3D modeling system, or machined. In other embodiments, some or all of the shaft 222, the nut or protruding member 224 and the head portion 226 are separate elements that are connected together in a fixed relation to each other.

The moving mechanism 220 is configured operate similar to the moving mechanism 20 described with respect to FIGS. 1-7, to selectively move the baked powder stick or pellet within the base portion component 212a1 in response to a manual rotation (about the axis A) of the base portion component 212a2 relative to the base portion component 212a1. In particular embodiments, rotation of the base portion component 212a2 in a first rotary direction about the axis A (one of counterclockwise or clockwise) causes the moving mechanism 220 to move the baked powder stick or pellet in first linear direction along the axis A, to extend or further extend the baked powder stick or pellet through the open end (cap end) of the base portion component 212a1. In this manner, a user may manually rotate the base portion component 212a2 in a first direction to adjust the distance that the baked powder stick or pellet extends from the base portion 212a of the housing 212.

In certain embodiments, the moving mechanism 220 is configured to allow movement of the baked powder stick or pellet in only one direction (e.g., a direction to further extend the baked powder stick or pellet from the base portion 212a of the housing 212). In other embodiments, the moving mechanism is configured to also allow movement of the baked powder stick or pellet in a second direction along the axis A (e.g., a direction to retract the baked powder stick or pellet further into the base portion 212a of the housing 212).

The shaft 222 of the moving mechanism 220 is configured to threadingly engage the base portion component 212a2 (for example, but not limited to, an engagement similar to the manner in which the moving mechanism 20 engages the base portion component 12a2 in the embodiment of FIGS. 1-7). The base portion component 212a2 is configured to connect with the base portion component 212a1 in a rotary manner, such that the base portion component 212a2 can be manually rotated (about the axis A) relative to the base portion component 212a1. In particular embodiments, the base portion component 212a2 includes one or more annular ribs 234 (for example, similar to the annular ribs 34 in FIGS. 1-7), configured to connect with the base portion component 212a1 in a manner similar to the manner in which the base portion component 12a2 connects with the base portion component 12a1 in the embodiment of FIGS. 1-7. In other embodiments other suitable mechanisms may be employed for connecting the base portion component 212a2 to the base portion component 212a2, and allow rotation of the base portion component 212b2 relative to the base portion component 212a1.

In the embodiment of FIG. 18, the base portion component 212a2 has ratchet teeth 239 (similar to ratchet teeth 39 in the embodiment of FIGS. 1-7) or other engagement surfaces that engage corresponding features on the inner surface of the base portion component 212a1, to inhibit rotation about the axis A of the base portion component 212a2 relative to the base portion component 212a1 in one direction (e.g., a clockwise direction), but allows relative rotation in the other direction (e.g., a counterclockwise direction). In other embodiments, such ratchet teeth or other engagement features are omitted, allowing relative rotation in both directions. In yet other embodiments the relative positions of the ratchet teeth and engagement features are reversed such that the ratchet teeth are on the inner surface of the base portion component 212a1, while the further engagement features are on the base portion component 212a2.

The base portion component 212a2 of the embodiment of FIG. 18 has a hollow, cylindrical interior volume that is open on one end (the upper end in FIG. 18) for receiving at least a portion of the shaft 222 of the moving mechanism 220. The inner surface of the hollow interior of the base portion component 212a2 is threaded to match (and threadingly engage) the threads on the shaft 222 of the moving mechanism 220.

When a portion of the shaft 222 is threadingly received within the hollow interior of the base portion component 212a2, a further portion of the shaft 222 (e.g., a portion with the nut or protruding member 224 and head 226) extend inside of the hollow interior of the base portion component 212a1. The outer surface of the nut or protruding member 224 and the outer surface of the head portion 226 of the moving mechanism 220 are arranged to abut an inner surface of the base portion component 212a1. As discussed above, in particular embodiments, the inner surface of the base portion component 212a1 is configured to match or engage with nut or protruding member 224 in a manner that inhibits relative rotation of the moving mechanism 220 about the axis A, relative to the base portion component 212a1 of the housing 212.

Accordingly, when the base portion component 212a2 is rotated (about the axis A) relative to the base portion component 212a1 in one direction (e.g., a counterclockwise direction), the moving mechanism 220 is inhibited from rotating relative to the base portion component 212a2, and, thus, is moved linearly in the direction of axis A (due to the threaded interface between the moving mechanism 220 and the base portion component 212a2. In particular embodiments, the threads on the interface between the moving mechanism 220 and the base portion component 212a1 are configured such that rotation of the base portion component 212a2 about the axis A in a first direction (e.g., counterclockwise) causes the moving mechanism 220 to move in a direction to extend the baked powder stick or pellet outward from or further outward from the open end (cap end) of the base portion component 212a1. As discussed above, further embodiments are configured such that rotation of the base portion component 212a2 about the axis A in a second direction (e.g., clockwise) causes the moving mechanism 220 to move in a direction to retract the baked powder stick or pellet inward through the first open end of the base portion component 212a1, while other embodiments are configured to inhibit rotation of the base portion component 212a2 about the axis A in the second direction.

As the moving mechanism 220 moves in a direction to extend the baked powder stick or pellet outward from or further outward, the moving mechanism 220 pushes against an end of the baked powder stick or pellet, to move the baked powder stick or pellet along the axis A, within the interior of the base portion component 212a1. In particular embodiments, one or more stabilizing members is provided to help stabilize the baked powder stick or pellet from moving in a direction transverse (or lateral) to the axis A, while still allowing the baked powder stick or pellet to be selectively moved (by the moving mechanism 220) in a direction of the axis A.

Figure 20:
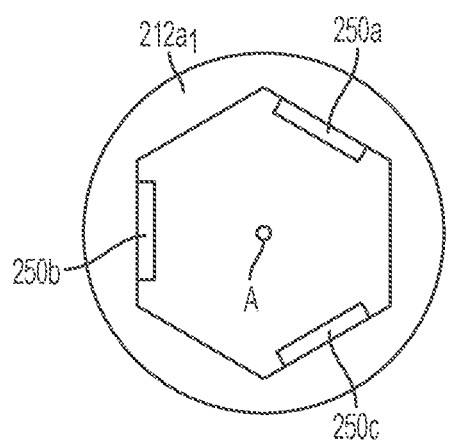
FIG. 20 is a cross-section view of a base portion component of the baked powder pencil of FIG. 18.
Figure 21:
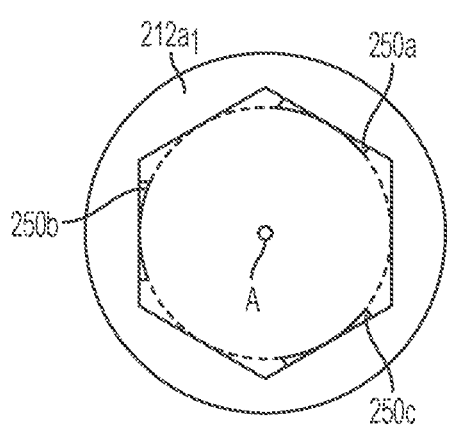
FIG. 21 is a cross-section view of a base portion component of the baked powder pencil of FIG. 18, with a baked powder stick or pellet located within the base portion component.

For example, with reference to FIGS. 20 and 21, cross-sectional views (taken perpendicular to the axis A) of an embodiment of a base portion component 212a1 having stabilizing members 250a, 250b and 250c is shown. In the embodiment of FIGS. 20 and 21, the interior surface of the base portion component 212a1 has a generally hexagonal cross-section shape that defines six flat surfaces around the axis A. The stabilizing members 250a, 250b and 250c are arranged on three of the six flat surfaces, at equal spacing from each other. In other embodiments, more or less than three stabilizing members may be employed. For example, in further embodiments, a separate stabilizing member is provided on each of the six flat surfaces. In yet other embodiments that employ base portion component 212a1 having other interior cross-sectional shapes (other than hexagonal), other arrangements of one or more stabilizing members may be employed.

In certain embodiments, the one or more stabilizing members include one or more cushioning members provided within the interior of the base portion component 212a1. Such cushioning members may be formed of a strip or pad of relatively soft or cushioning material, such as, but not limited to a foam, rubber, silicon, felt, fabric, or other suitable material, arranged along one or more interior surfaces of the base portion component 212a1. In particular embodiments, one or more of such strips or pads of cushioning members are adhered to one or more interior surfaces of the base portion component 212a1, by any suitable adhesive including, but not limited to a glue, double-sided tape, heat weld, or the like. In other embodiments, the one or more stabilizing members are molded with or otherwise formed on the base portion component 212a1, for example, as a unitary structure with the base portion component 212a1.

With reference to FIGS. 18-21, the stabilizing members 250a, 250b and 250c are arranged on a portion of the interior surface(s) of the base portion component 212a1 located near the open end (cap end) of the base portion component 212a1, but spaced from the open end (or cap end). In particular embodiments, the stabilizing members 250a, 250b and 250c are spaced from the open end (or cap end) by a lip or ring-shaped portion 252 of the base portion component 212a1, at the open end (cap end) of the base portion component 212a1. In certain embodiments, the lip or ring-shaped portion 252 may have an inner diameter that is about tangent to or slightly larger than the diameter defined by the flat surfaces of the hexagonal-shaped interior surface of the base portion component 212a1. (e.g., corresponding to, or slightly larger than the broken circle shown in FIG. 21).

In certain embodiments, the ring-shaped portion 252 of the base portion component 212a1 is molded with or otherwise formed integral with the rest of the base portion component 212a1. In other embodiments, the ring-shaped portion 252 of the base portion component 212a1 is formed separate from the base portion component 212a1 and is subsequently attached to the base portion component 212a1 by glue, welding or any other suitable attachment mechanism. In particular embodiments, the stabilizing members 250a, 250b and 250c are located on the interior surface(s) of the base portion component 212a1 at a position above the nut or protruding member 224 of the moving mechanism 220 (between the nut or protruding member 224 and the open or cap end of the base portion component 212a1), so as not to be engaged by the nut or protruding member 224 throughout the entire range of movement of the moving mechanism 220 within the base portion component 212a1. Accordingly, as shown in FIG. 18-21, in particular embodiments, the stabilizing members 250a, 250b and 250c are located between the ring-shaped portion 252, and the highest possible location (on the axis A) of the nut or protruding member 224 (along the range of motion of the moving mechanism 220).

With reference to FIG. 21, when the baked powder stick or pellet is located within the base portion component 212a1, the outer surface of the baked powder stick or pellet is in contact with one or more (or each of) the stabilizing members 250a, 250b and 250c. In particular, the stabilizing members 250a, 250b and 250c inhibit lateral movement (transverse to the direction of the axis A) of the baked powder stick or pellet, when the moving mechanism moves the baked powder stick or pellet in the direction of the axis A. In embodiments in which the stabilizing members 250a, 250b and 250c are composed of a resilient cushioning material, the outer surface of the baked powder stick or pellet (represented by the broken lines in FIG. 21) may press against and partially deform one or more (or each of) the stabilizing members 250a, 250b and 250c. Accordingly, the stabilizing members 250a, 250b and 250c can provide a lateral support or force that gently inhibits lateral motion (transverse to the axis A) and helps to protect the baked powder stick or pellet from damage, while also allowing the baked powder stick or pellet to be selectively moved, linearly, along the axis A by the moving mechanism 220.

In addition to, or as an alternative to, one or more stabilizing members, the base portion component 212a1 is configured with one or more retention features to help retain the baked powder stick or pellet in the base portion component 212a1. In particular embodiments, such retention features include one or more (or a plurality of) projections 240 extending inward (toward the axis A) from an inner surface of the ring-shaped portion 252 of the base portion component 212a1. The projections 240 may be similar to the ramp shaped projections 40 in the embodiment of FIGS. 1-7. In such embodiments, the tapered surface of each ramp-shaped projection 240 allows the baked powder stick or pellet to be moved in the extending direction (i.e., upward in the direction of FIGS. 18 and 19), but inhibits movement of the baked powder stick or pellet in a retraction direction (i.e., downward in the direction of FIGS. 18 and 19). In particular embodiments, three projections are arranged around the axis A, each at a 120 degree spacing from adjacent projections. However, in other embodiments, more or less than three projections may be arranged around the axis A.

The embodiment in FIGS. 18-21 includes a base portion component 212a1 that has an open end (cap end) having an annular edge that is generally perpendicular to the axis A. However, in other embodiments, the annular edge of the open end (cap end) of the base portion component 212a1 is configured at an oblique or inclined angle relative to the axis A, for example, but not limited to the inclined, angled annular edge 128a2 of the guide member 128 in the embodiment of FIGS. 8-17. In such embodiments, a single (or at least one) projection 240 is arranged on the inner surface of the base portion component 212a1 (or the inner surface of the ring-shaped portion 252) at a location adjacent and just below the lower side of the angled, annular edge (i.e., corresponding to the right side of the annular edge 128a2 in the view orientation shown in FIGS. 8-17). In such embodiments, the projection 240 forces the baked powder stick or pellet toward the longer inner surface of the base portion component 212a1 (i.e., on the left side of the interior of the guide member 128 in the orientation of FIG. 8). In such embodiments, the projection 240 and the longer side of the interior wall of the base portion component 212a1 can operate together, for additional stability and retention of the baked powder stick or pellet within the base portion component 212a1.

Figure 22:
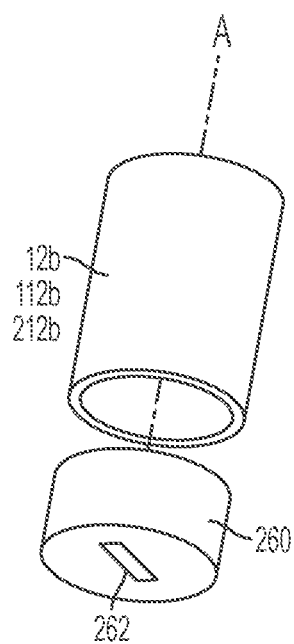
FIG. 22 is a perspective view of an embodiment of a cap for a baked powder pencil.
Figure 23:
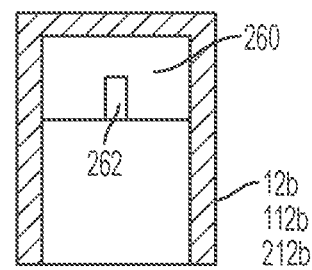
FIG. 23 is a cross-section view of the cap of FIG. 22.

The embodiments in FIGS. 1-21 include a cap 12b, 112b and 212b. In other embodiments, the cap may be omitted. In yet other embodiments, the cap 12b, 112b and 212b may include a cushion feature, such as, but not limited to a cushion insert 260 as shown in FIGS. 22 and 23. In particular embodiments, the cushion insert comprises a soft or resilient cushioning material, such as, but not limited to a foam, rubber, silicon, felt, fabric, or other suitable material. In particular embodiments, the cushion insert is configured as a separate element that is inserted into and adhered to the interior of the cap 12b, 112b or 212b. The cushion insert can provide additional stability and protection for an extended end of the baked powder stick or pellet. In particular embodiments, the cushion insert includes a slot, slit, indentation or recess 262 that receives a portion (e.g., tip end) of the end of the baked powder stick or pellet, when the cap 12b, 112b or 212b is installed onto the base portion 12a, 112a or 212a. In further embodiments, the cushion insert may have sufficient rigidity to provide a honing, shaping or sharpening action on the tip end of the baked powder stick or pellet, to help reform a desired shape of the tip end, when the cap 12b, 112b or 212b is installed onto the base portion 12a, 112a or 212a.

The preceding description of the disclosed embodiments is provided to enable any person skilled in the art to make or use the present invention. Various modifications to these embodiments will be readily apparent to those skilled in the art, and the generic principles defined herein may be applied to some embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A baked powder pencil comprising:
   a housing having a base portion with a hollow interior and an opening that opens into the hollow interior; and
   a stick or pellet of baked powder cosmetic material disposed at least partially within the hollow interior of the base portion, the stick or pellet of baked powder cosmetic material having an end portion that is arranged to extend through the opening of the base portion;
   wherein the stick or pellet of baked powder cosmetic material comprises a material that is formed into a pre-defined three-dimensional shape when baked, and is configured to maintain its three-dimensional shape without external support while the end portion of the stick or pellet of baked powder cosmetic material extends through the opening of the base portion.

2. A baked powder pencil as recited in claim 1, wherein the stick or pellet of baked powder cosmetic material comprises a baked powder material composed of one or more coloring agents to provide a desired color and tone, a skin care agent, or a binding agent.

3. A baked powder pencil as recited in claim 1, wherein the stick or pellet of baked powder cosmetic material is formed into a pre-defined three-dimensional, generally cylindrical shape having a head section to be applied to a user's skin and a distal end section that is held within the hollow interior of the base portion of the housing.

4. A baked powder pencil as recited in claim 1, wherein the stick or pellet of baked powder cosmetic material comprises a three-dimensional molded, extruded or shaped body of baked powder material.

5. A baked powder pencil as recited in claim 1, wherein the base portion of the housing includes a moving mechanism configured to selectively move the stick or pellet of baked powder cosmetic material through the opening of the base portion to adjust a distance that the stick or pellet of baked powder cosmetic material extends past the opening of the base portion of the housing.

6. A baked powder pencil as recited in claim 5, wherein the moving mechanism is configured to selectively move the stick or pellet of baked powder material in one direction to selectively extend the stick or pellet of baked powder cosmetic material further past the opening of the base portion housing and inhibits movement of the stick or pellet of baked powder cosmetic material in an opposite direction that would retract the stick or pellet of baked powder cosmetic material further into the base portion of the housing.

7. A baked powder pencil as recited in claim 5, wherein:
the base portion of the housing includes at least one projection arranged adjacent the opening of the base portion, the at least one projection arranged to project into a body section of the stick or pellet of baked powder cosmetic material; and
the moving mechanism is configured to selectively move the stick or pellet of baked powder cosmetic material in one direction to selectively extend the stick or pellet of baked powder cosmetic material further past the opening of the base portion housing and inhibits movement of the stick or pellet of baked powder cosmetic material in an opposite direction that would retract the stick or pellet of baked powder cosmetic material further into the base portion of the housing.

8. A baked powder pencil as recited in claim 7, wherein:
the opening of the base portion of the housing has an annular edge that is angled at an oblique angle relative to the one direction at which the moving mechanism selectively moves the stick or pellet of baked powder cosmetic material, the annular edge having a first edge portion that is closer an end of the base portion opposite to the opening than a second edge portion; and
the at least one projection is arranged on an interior surface of the base portion, adjacent the first edge portion of the annular edge.

9. A baked powder pencil as recited in claim 7, wherein the at least one projection is configured with a shape that allows movement of the stick or pellet of baked powder cosmetic material in the one direction and inhibits movement of the stick or pellet of baked powder cosmetic material in the opposite direction.

10. A baked powder pencil as recited in claim 9, wherein the at least one projection has a tapered surface facing into the base portion of housing, the tapered surface arranged to cut into the body section of the stick or pellet of baked powder cosmetic material as the stick or pellet of baked powder cosmetic material is moved in the one direction.

11. A baked powder pencil as recited in claim 5, further comprising at least one stabilizing member arranged within the hollow interior of the base portion to minimize or inhibit movement of the baked powder stick or pellet in a direction transverse to a direction at which the moving mechanism selectively moves the stick or pellet of baked powder cosmetic material.

12. A baked powder pencil as recited in claim 11, wherein the at least one stabilizing member comprises at least one of: (a) at least one pad of resilient cushioning material, or (b) a plurality of pads of material each arranged at an equal distance from adjacent pads around an axis of the base portion of the housing.

13. A baked powder pencil as recited in claim 11, wherein the base portion has an interior surface having a polygonal cross-section shape and wherein the at least one stabilizing member comprises a plurality of stabilizing members, each arranged on a different respective flat surface of the polygonal cross-section shape of the interior surface.

14. A baked powder cosmetic, comprising: a baked powder cosmetic material formed in a stick or pellet having a three-dimensional shape when baked, and configured to maintain its three-dimensional shape without external support, when baked.

15. A baked powder cosmetic as recited in claim 14, wherein the baked powder cosmetic material includes one or more coloring agents to provide a desired color and tone, a skin care agent, or a binding agent.

16. A baked powder cosmetic as recited in claim 14, wherein the baked powder stick or pellet is formed into a pre-defined three-dimensional, generally cylindrical shape having a head section configured to be applied to a user's skin, and a distal end section that is held within a housing.

17. A baked powder cosmetic as recited in claim 14, wherein the three-dimensional shape of the stick or pellet of baked powder cosmetic material comprises a head section having multiple, generally planar surfaces extending in multiple respectively different planes.

18. A baked powder cosmetic as recited in claim 17, wherein the multiple different planes extend at multiple different respective oblique angles relative to each other.

19. A baked powder cosmetic as recited in claim 18, wherein the three-dimensional shape of the stick or pellet of baked powder cosmetic material comprises a body section having a generally cylindrical or semi-cylindrical surface extending along an axis A, and wherein the multiple planes extend at multiple different respective oblique angles relative to the axis A.

20. A baked powder cosmetic as recited in claim 14, wherein the three-dimensional shape of the stick or pellet of baked powder cosmetic material comprises a head section having a semi-spherical or semi-spheroid shaped surface configured to be applied to a user's skin.

21. A baked powder cosmetic as recited in claim 14, further comprising a housing having a base portion with a hollow interior and an opening that opens into the hollow interior, wherein the three-dimensional shape of the stick or pellet of baked powder cosmetic material is supported at least partially within the hollow interior of the base portion of the housing, with the head section arranged to extend at least partially out from the opening of the base portion of the housing.

22. A baked powder cosmetic as recited in claim 14, wherein the three-dimensional shape of the stick or pellet of baked powder cosmetic material comprises a head section having a semi-spherical or semi-spheroid shaped surface, a body section having a generally cylindrical surface, and a tapered surface extending from the generally cylindrical surface of the body section to the semi-spherical or semi-spheroid shaped surface of the head section.

23. A method of making a baked powder cosmetic comprising forming a baked powder cosmetic material in a stick or pellet having a three-dimensional shape and configured to maintain its three-dimensional shape without external support, when baked; baking the baked powder cosmetic material to maintain the three-dimensional shape when baked; and supporting the stick or pellet in a housing, with a head section of the stick or pellet extending through an opening in the housing, while a body portion of the stick or pellet is contained within the housing.

* * * * *